US011780892B2

(12) United States Patent
McBride et al.

(10) Patent No.: US 11,780,892 B2
(45) Date of Patent: Oct. 10, 2023

(54) CHIMERIC IMMUNOGENIC POLYPEPTIDES

(71) Applicant: Research Development Foundation, Carson City, NV (US)

(72) Inventors: Jere W. McBride, Galveston, TX (US); David H. Walker, Galveston, TX (US)

(73) Assignee: Research Development Foundation, Carson City, NV (US)

(*) Notice: Subject to any disclaimer, the term of this patent is extended or adjusted under 35 U.S.C. 154(b) by 246 days.

(21) Appl. No.: 17/331,518

(22) Filed: May 26, 2021

(65) Prior Publication Data
US 2021/0292377 A1    Sep. 23, 2021

Related U.S. Application Data

(62) Division of application No. 16/524,446, filed on Jul. 29, 2019, now Pat. No. 11,046,734.

(60) Provisional application No. 62/711,005, filed on Jul. 27, 2018.

(51) Int. Cl.
*A61K 39/00* (2006.01)
*C07K 14/29* (2006.01)
*A61K 39/02* (2006.01)
*G01N 33/569* (2006.01)
*G01N 33/68* (2006.01)

(52) U.S. Cl.
CPC .......... *C07K 14/29* (2013.01); *A61K 39/0233* (2013.01); *G01N 33/56911* (2013.01); *G01N 33/6854* (2013.01); *C07K 2319/33* (2013.01)

(58) Field of Classification Search
CPC .................................................... C07K 14/29
See application file for complete search history.

(56) References Cited

U.S. PATENT DOCUMENTS

| | | | |
|---|---|---|---|
| 7,344,893 B2 | 3/2008 | Kirkegaard et al. | |
| 8,980,288 B2 | 3/2015 | Diehl et al. | |
| 9,545,439 B2 | 1/2017 | Diehl et al. | |
| 9,662,385 B2 | 5/2017 | Dominowski et al. | |
| 10,001,699 B2 | 6/2018 | Orihara et al. | |
| 10,117,921 B2 | 11/2018 | Dominowski et al. | |
| 2002/0177178 A1 | 11/2002 | Lawton et al. | |
| 2006/0234322 A1 | 10/2006 | Krah, III et al. | |
| 2010/0273194 A1 | 10/2010 | McBride | |
| 2010/0330091 A1 | 12/2010 | McBride et al. | |
| 2012/0219972 A1 | 8/2012 | Thomas et al. | |
| 2019/0038737 A1 | 2/2019 | Dominowski et al. | |
| 2020/0026178 A1 | 1/2020 | Jindal et al. | |
| 2020/0133111 A1 | 4/2020 | Liu et al. | |

FOREIGN PATENT DOCUMENTS

| | | |
|---|---|---|
| EP | 2433646 | 3/2012 |
| TW | 201921086 A | 6/2019 |
| TW | 202008073 A | 2/2020 |
| TW | 202026770 A | 7/2020 |
| WO | WO1998/042740 | 10/1998 |
| WO | WO2000/000615 | 1/2000 |
| WO | WO2002/057794 | 7/2002 |
| WO | WO2005/087803 | 9/2005 |
| WO | WO 2008/043000 | 4/2008 |
| WO | WO 2009/034575 | 3/2009 |
| WO | WO 2011/125015 | 10/2011 |

OTHER PUBLICATIONS

Dumler et al., "Ehrlichioses in humans: epidemiology, clinical presentation, diagnosis, and treatment," Clin. Infect. Dis., 45:S45-S51, 2007.
Partial European Search Report for EP Appl. No. 19842185.1 dated Mar. 25, 2022, 13 pages.
Extended European Search Report for EP Appl. No. 19842185.1 dated Jun. 28, 2022, 13 pages.
Feng and Walker, "Mechanisms of immunity to Ehrlichia muris: a model of monocytotropic ehrlichiosis," Infect. Immun., 72:966-971, 2004.
Fishbein et al., "Human ehrlichiosis in the United States, 1985 to 1990," AnnInternMed 120:736-743, 1994.
He et al., "Vaxign: the first web-based vaccine design program for reverse vaccinology and applications for vaccine development," J Biomed Biotechnol 2010:297505, 2010.
International Search Report for PCT/US19/43840, dated Dec. 6, 2019.
Kuriakose et al., "Ehrlichia chaffeensis transcriptome in mammalian and arthropod hosts reveals differential gene expression and post transcriptional regulation," PLoS One 6:e24136, 2011.
Kuriakose et al., "Molecular basis of antibody mediated immunity against Ehrlichia chaffeensis invol

(56) References Cited

OTHER PUBLICATIONS

Lou et al., "Major Species-Specific Antibody Epitopes of the Ehrlichia chaffeensis p120 and E-canis p140 Orthologs in Surface-Exposed Tandem Repeat Regions", *Clinical and Vaccine Immun*, 16(7), 982-990, 2009.

Magnan et al., "High-throughput prediction of protein antigenicity using protein microarray data," Bioinformatics 26:2936-2943, 2010.

McBride and Walker, "Progress and obstacles in vaccine development for the ehrlichioses," Expert Rev Vaccines 9:1071-1082, 2010.

Nandi et al., "CD4 T-cell epitopes associated with protective immunity induced following vaccination of mice with an ehrlichial variable outer membrane protein," InfectImmun 75:5453-5459., 2007.

Olano et al., "Human monocytotropic ehrlichiosis, Missouri," EmergInfectDis 9:1579-1586, 2003.

Paparone et al., Ehrlichiosis with pancytopenia and ARDS. New Jersey Med 92:381-385, 1995.

Racine et al., "IgM production by bone marrow plasmablasts contributes to long-term protection against intracellular bacterial infection," J Immunol 186:1011-1021, 2011.

Sotomay et al., "Animal model of fatal human monocytotropic ehrlichiosis," AmJPath 158:757-769, 2001.

Stuen et al., "Lambs Immunized with an Inactivated Variant of Anaplasma Phagocytophilum," *Acta Vet Scand.*, 57:40, 2015.

Tollersrud et al., "*Staphylococcus aureus* Capsular Polysaccharide Type 5 Conjugate and Whole Cell Vaccines Stimulate Antibody Responses in Cattle," *Vaccine*, 19:3896-3903, 2001.

Vega et al., "Anaplasma Marginale Field Challenge: Protection by an Inactivated Immunogen that Shares Partial Sequence of Msp1alpha Variable Region with the Challenge Strain," *Vaccine*, 25:519-525, 2007.

Walker and Dumler, "Human monocytic and granulocytic ehrlichioses. Discovery and diagnosis of emerging tick-borne infections and the critical role of the pathologist," [Review] [50 refs]. Archives of Pathology & Laboratoiy Medicine 121:785-791, 1997.

Walker et al., "Ehrlichia chaffeensis: a prevalent, life-threatening, emerging pathogen," Trans Am Clin Climatol Assoc 115:375-382; discussion 382-374, 2004.

Winslow et al., "Infection of the laboratory mouse with the intracellular pathogen *Ehrlichia chaffeensis*," InfectImmun 66:3892-3899, 1998.

Winslow et al., "Antibody-Mediated Elimination of the Obligate Intracellular Bacterial Pathogen Ehrlichia Chaffeensis During Active Infection," *Infect. Immun.*, 68:2187-2195, 2000.

Winslow et al., "Mechanisms of Humoral Immunity During Ehrlichia Chaffeensis Infection," *Ann. NY Acad. Sci.*, 990:435-443, 2003.

Yager et al., "Essential Role for Humoral Immunity During Ehrlichia Infection in Immunocompetent Mice," *Infect. Immun.*, 73:8009-8016, 2005.

*E.chaffeensis* Chimera

Name: *E.chaff* TRP32/TRP120/A34
  32R1 / 32R2 / 32R3 / 32R4 / 3x120 / 3xA34N1
  TRP32R1: SDLHESSFVELPGPSKEEVQFEDDAKNVVY    TRP32R2: SDLHGSFSVELFDPSKEEVQLESDLQQSSN
  TRP32R3: SDLHGSFSVELFDPFKEAVQLGNDLQQSSD    TRP32R4: SDSHEPSHLELPSLSEEVIQLESDLQQSSN
  TRP120: SKVEQEETNPEVLIKDLQDVA              A34N1: VRSITDPRIVVQQEADQQQEVQQQAD Sequence:
  SDLHESSFVELPGPSKEEVQFEDDAKNVVYSDLHGSFSVELFDPSKEEVQLESDLQQSSNSDLHGSFSVE
  LFDPFKEAVQLGNDLQQSSDSDSHEPSHLELPSLSEEVIQLESDLQQSSNGGGSKVEQEETNPEVLIKDL
  QDVASSKVEQEETNPEVLIKDLQDVASSKVEQEETNPEVLIKDLQDVASGGGVRSITDPRIVVQQEADQQ
  QEVQQQADVRSITDPRIVVQQEADQQQEVQQQADVRSITDPRIVVQQEADQQQEVQQQAD Expression / Purification / Western Blot: (Tag: His; Vector: pET-14b; Expression cells: BL21-DE3)

Expression of *E.chaff* chimera    Purified *E.chaff* chimera    Reacting with anti-*E.chaff* serum Reacting with human patient sera:

FIG. 1

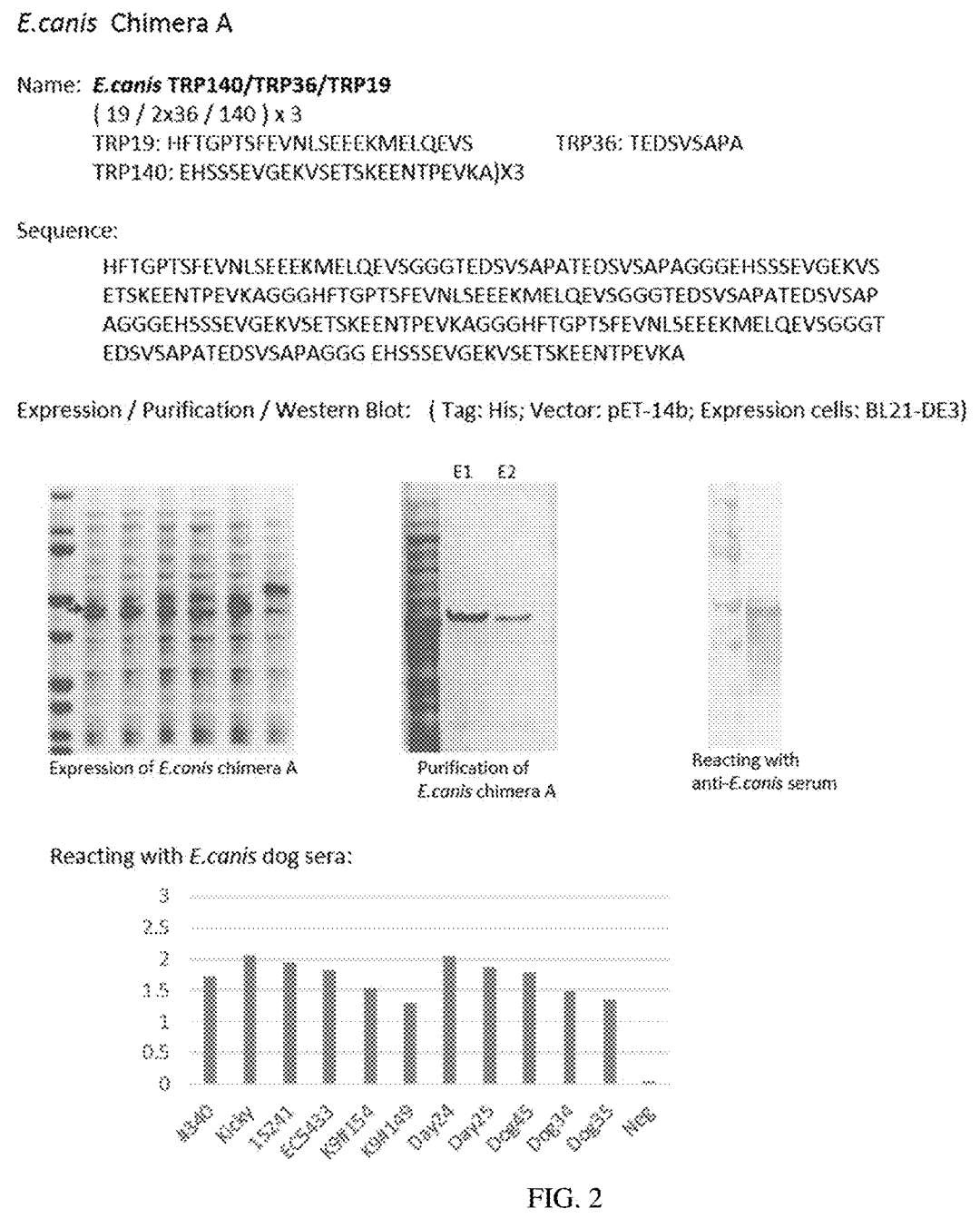

*E.canis* Chimera A

Name: *E.canis* TRP140/TRP36/TRP19
    ( 19 / 2x36 / 140 ) x 3
    TRP19: HFTGPTSFEVNLSEEEKMELQEVS &nb

*E. canis* Chimera B

Name: *E.canis* TRP36/TRP140
    8x36 / 4x140
    TRP36: TEDSVSAPA   TRP140: EHSSSEVGEKVSETSKEENTPEVKA Sequence:
TEDSVSAPATEDSVSAPATEDSVSAPATEDSVSAPATEDSVSAPATEDSVSAPATEDSVSAPATEDSVSAPA
GGGEHSSSEVGEKVSETSKEENTPEVKAEHSSSEVGEKVSETSKEENTPEVKAEHSSSEVGEKVSETSKEENT
PEVKAEHSSSEVGEKVSETSKEENTPEVKA Expression / Purification / Western Blot: ( Tag: His; Vector: pET-14b; Expression cells: BL21-AI)

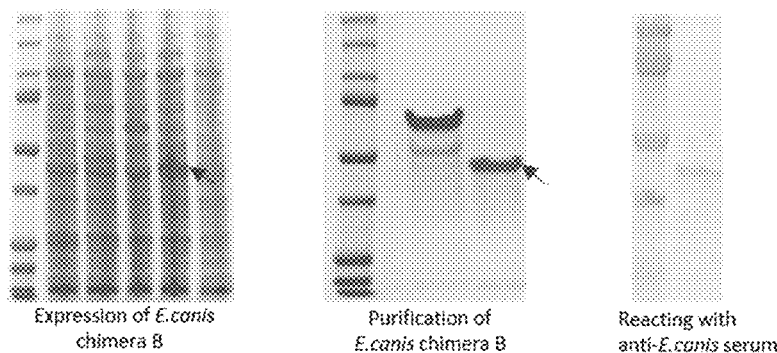

Expression of *E.canis* chimera B    Purification of *E.canis* chimera B    Reacting with anti-*E.canis* serum Reacting with *E.canis* dog sera:

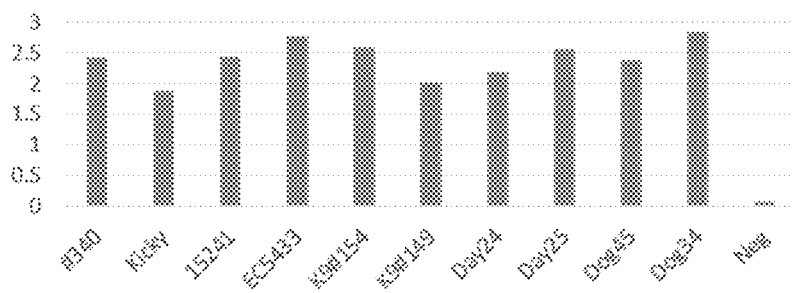

FIG. 3

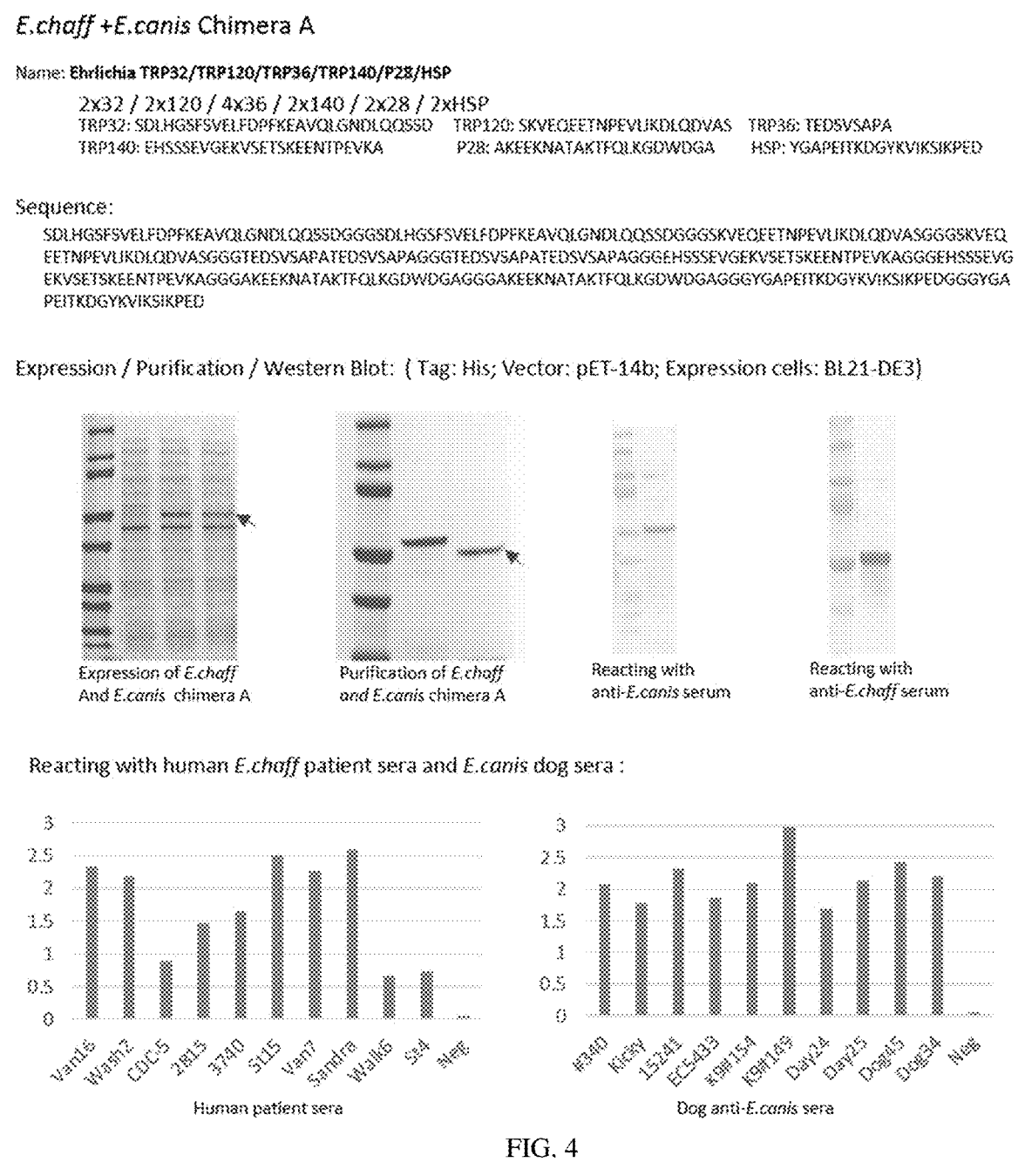

*E.chaff* +*E.canis* Chimera A

Name: Ehrlichia TRP32/TRP120/TRP36/TRP140/P

E.chaff +E.canis Chimera B

Name: Ehrlichia TRP120/TRP140/TRP36/p28
   3x120 / 3x140 / 6x36 / 3x28
   TRP120: SKVEQEETNPEVLIKDLQDVAS   TRP140: EHSSSEVGEKVSETSKEENTPEVKA
   TRP36: TEDSVSAPA                 P28: AKEEKNATAKTFQLKGDWDGA Sequence:
   SKVEQEETNPEVLIKDLQDVASSKVEQEETNPEVLIKDLQDVAS SKVEQEETNPEVLIKDLQDVASGGGEHSSSEVGEKVSETSKEENTPEVKA
   EHSSSEVGEKVSETSKEENTPEVKAEHSSSEVGEKVSETSKEENTPEVKAGGGTEDSVSAPATEDSVSAPATEDSVSAPATEDSVSAPATEDSVS
   APATEDSVSAPAGGGAKEEKNATAKTFQLKGDWDGA AKEEKNATAKTFQLKGDWDGAAKEEKNATAKTFQLKGDWDGA Expression / Purification / Western Blot: (Tag: His; Vector: pET-14b; Expression cells: BL21-AI)

Expression of E.chaff And E.canis chimera A | Purification of E.chaff and E.canis chimera A | Reacting with anti-E.canis serum | Reacting with anti-E.chaff serum Reacting with human E.chaff patient sera and E.canis dog sera:

Human patient sera | Dog anti-E.canis sera

FIG. 5

**Name: *E.chaff* 120/34/63/47**
    2x120/2x34/2x63/2x47
 120: SKVEQEETNPEVLIKDLQDVAS (SEQ ID NO: 22) 34: VRSITDPRIVVQQEADQQQEVQQQAD (SEQ ID NO: 7)
  63: SLFTEEEKILAILSARFICK (SEQ ID NO: 18)    47: ASVSEGDAVVNAVSQETPA (SEQ ID NO: 17)

Sequence:
    SKVEQEETNPEVLIKDLQDVASSKVEQEETNPEVLIKDLQDVASGGG
    VRSITDPRIVVQQEADQQQEVQQQADVRSITDPRIVVQQEADQQQEVQQQADGGG
    SLFTEEEKILAILSARFICKSLFTEEEKILAILSARFICKGGGASVSEGDAVVNAVSQETPA
    ASVSEGDAVVNAVSQETPA (SEQ ID NO: 30)

**Name: *E.chaff* 120/34/63**
    2x120/2x34/2x63
120: SKVEQEETNPEVLIKDLQDVAS (SEQ ID NO: 22)  34: VRSITDPRIVVQQEADQQQEVQQQAD (SEQ ID NO: 7)
    63: SLFTEEEKILAILSARFICK (SEQ ID NO: 18)

Sequence:
    SKVEQEETNPEVLIKDLQDVASSKVEQEETNPEVLIKDLQDVASGGG
    VRSITDPRIVVQQEADQQQEVQQQADVRSITDPRIVVQQEADQQQEVQQQADGGG
    SLFTEEEKILAILSARFICKSLFTEEEKILAILSARFICK (SEQ ID NO: 31)

**Name: *E.chaff* 120/34/47**
    2x120/2x34/2x63/2x47
 120: SKVEQEETNPEVLIKDLQDVAS (SEQ ID NO: 22)  34: VRSITDPRIVVQQEADQQQEVQQQAD (SEQ ID NO: 7)
    47: ASVSEGDAVVNAVSQETPA (SEQ ID NO: 17)

Sequence:
    SKVEQEETNPEVLIKDLQDVASSKVEQEETNPEVLIKDLQDVASGGG
    VRSITDPRIVVQQEADQQQEVQQQADVRSITDPRIVVQQEADQQQEVQQQAD
    GGGASVSEGDAVVNAVSQETPA ASVSEGDAVVNAVSQETPA (SEQ ID NO: 32)

**Name: *E.chaff* 34/63/47**
    2x34/2x63/2x47
34: VRSITDPRIVVQQEADQQQEVQQQAD (SEQ ID NO: 7) 63: SLFTEEEKILAILSARFICK    (SEQ ID NO: 18)
    47: ASVSEGDAVVNAVSQETPA (SEQ ID NO: 17)

Sequence:
    VRSITDPRIVVQQEADQQQEVQQQADVRSITDPRIVVQQEADQQQEVQQQADGGG
    SLFTEEEKILAILSARFICKSLFTEEEKILAILSARFICKGGGASVSEGDAVVNAVSQETPA
    ASVSEGDAVVNAVSQETPA (SEQ ID NO: 33)

**Name: *E.chaff* 34/63/75**
    2x34/2x63/2x75
    34: VRSITDPRIVVQQEADQQQEVQQQAD (SEQ ID NO: 7)  63: SLFTEEEKILAILSARFICK  (SEQ ID NO: 18)
    75: DVKDNKPSDVKLPVIKAE (SEQ ID NO: 19)

Sequence:
    VRSITDPRIVVQQEADQQQEVQQQADVRSITDPRIVVQQEADQQQEVQQQADGGG
    SLFTEEEKILAILSARFICKSLFTEEEKILAILSARFICKGGGDVKDNKPSDVKLPVIKAE DVKDNKPSDVKLPVIKAE
    (SEQ ID NO: 34)

FIG. 6

Name: *E. canis* 36/140/95R/95C
    2x36/2x140/2x95R/2x95C
    36: TEDSVSAPA (SEQ ID NO: 8)    140: EHSSSEVGEKVSETSKEENTPEVKA (SEQ ID NO: 23)
    95R: DDSKLPVIKVEDKSKLQDTKDKKR (SEQ ID NO: 20)   95C: KKIKEYDEDYTITYYYDDD (SEQ ID NO: 21)

Sequence:
TEDSVSAPATEDSVSAPAGGGEHSSSEVGEKVSETSKEENTPEVKA
EHSSSEVGEKVSETSKEENTPEVKAGGGDDSKLPVIKVEDKSKLQDTKDKKR
DDSKLPVIKVEDKSKLQDTKDKKRGGGKKIKEYDEDYTITYYYDDD KKIKEYDEDYTITYYYDDD (SEQ ID NO: 35)

Name: *E. canis* TRP36 US/BR/Col
    2xUS/2xBR/2xIS/1XCol
    TRP36US: TEDSVSAPA (SEQ ID NO: 8)    TRP36BR: ASVVPEAE (SEQ ID NO: 9)
    TRP36CO: EASVVPAAEAPQPAQQTEDEFFSDGIEA (SEQ ID NO: 40)

Sequence:
TEDSVSAPATEDSVSAPAGGGASVVPEAEASVVPEAEGGGEA
SVVPAAEAPQPAQQTEDEFFSDGIEAEASVVPAAEAPQPAQQTEDEFFSDGIEA (SEQ ID NO: 43)

Name: *E. canis* TRP36 US/IS
    2xUS/2xIS
    TRP36US: TEDSVSAPA
    TRP36IS: TEDSPSATA Sequence:
TEDSVSAPATEDSVSAPAGGGTEDSPSATATEDSPSATA (SEQ ID NO: 44)

FIG. 6 (continued)

CHIMERIC IMMUNOGENIC POLYPEPTIDES

This application is a divisional of U.S. application Ser. No. 16/524,446, filed Jul. 29, 2019, which claims the benefit of U.S. Provisional Patent Application No. 62/711,005, filed Jul. 27, 2018, the entirety of each of which is incorporated herein by reference.

BACKGROUND OF THE INVENTION

1. Field of the Invention

The present invention relates generally to the field of molecular biology and medicine. More particularly, it concerns chimeric polypeptides that may be used for diagnostic or vaccination purposes.

2. Description of Related Art

Human monocytotropic ehrlichiosis (HME) is a group 1 NIAID emerging disease, and the etiologic agent, *E. chaffeensis*, is classified as a Category C priority pathogen. HME is an undifferentiated febrile illness that is life-threatening, clinical diagnosis is difficult, and definitive diagnosis is most often retrospective (Walker and Dumler, 1997; Walker et al., 2004; Dumler et al., 2007). Although well over 8,000 cases have been reported to the Centers for Disease Control as of 2012, this number likely underestimates the actual number of cases by 100-fold (Olano et al., 2003). The disease is often undiagnosed due to the non-specific symptoms associated with the onset, but it results in patient hospitalization in 43-62% of cases (Fishbein et al., 1994). Progression of the disease can result in a fatal outcome and often involves multisystem failure, with acute respiratory distress syndrome (ARDS) and meningoencephalitis being common in many fatal cases (Fishbein et al., 1994; Paparone et al., 1995). The threat to public health is increasing with newly emerging ehrlichial agents, yet vaccines for human ehrlichioses are not available, and therapeutic options are limited. New information and bioinformatics prediction tools have been developed that make a genome-wide identification of protective immunodiagnostic/vaccine candidates feasible (He et al., 2010; Magnan et al., 2010)

Prospects for development of effective subunit vaccines and immunodiagnostics for *Ehrlichia* have been limited due to many factors, not the least of which is the small repertoire of immunoreactive/protective proteins that have been molecularly defined (McBride and Walker, 2010). The gaps in knowledge required to address this problem for *Ehrlichia chaffeensis* have been narrowed by progress in understanding of protective/pathologic immune mechanisms (Feng and Walker 2004; Nandi et al., 2007; Winslow et al., 2000), immunomolecular characterization of some vaccine/diagnostic antigens (Kuriakose et al., 2012; Li et al., 2002), genome, transcriptome and proteome profiles (Kuriakose et al., 2011; Lin et al., 2011), new animal models (Winslow et al., 1998; Sotomay et al., 2001), and other technological advances. Studies utilizing low throughput approaches to define antigenic components of *E. chaffeensis* have yielded a small group of protective antigens that include a major outer membrane protein (OMP), and a family of secreted tandem repeat protein (TRP) effectors with major protective linear antibody epitopes (Kuriakose et al., 2012; Li et al., 2001). Nevertheless, these antigens likely represent a significant, but incomplete repertoire of immunoreactive/protective proteins. In addition, it is well established that antibody-mediated immunity is necessary for protection against *E. chaffeensis* infection (Winslow et al., 2000; Li et al., 2002; Kuriakose et al., 2012; Li et al., 2001; Racine et al., 2011; Yager et al., 2005), and antibodies are the cornerstone of the most effective vaccines for humans. Elimination of *E. chaffeensis* occurs, at least in part, during the extracellular stage of infection (Li and Winslow 2003); however, intracellular immune mechanisms may also be important, and defining the characteristics of antigens/antibodies that are protective in both environments is critical for effective vaccine development. Clearly, there is a need for new and improved methods for diagnosing and vaccinating against *E. chaffeensis* and *E. canis*.

SUMMARY OF THE INVENTION

The present disclosure, in some aspects, provides methods and compositions for the diagnosis of and vaccination against *Ehrlichia chaffeensis* (*E. chaffeensis*) and/or *Ehrlichia canis* (*E. canis*). In some embodiments, chimeric immunogenic peptides and polypeptides are provided. In some aspects, it has been discovered that contiguous repetition of different immunogenic sequences can be used to generate peptides or polypeptides that display improved properties for diagnosis and/or inducing immune responses against *E. chaffeensis* and/or *E. canis*.

As shown in the below examples, immunoreactive *E. chaffeensis* and *E. canis* peptides were used to produce chimeric *Ehrlichia* polypeptides. Chimeric polypeptides included in Table 2 were verified to be immunoreactive using ELISA tests on human monocytotropic ehrlichiosis (HME) positive human and canine sera. ELISA testing using positive HME sera obtained from patients revealed that the below constructs elicited significant responses, indicating that peptides (e.g., of Table 1) can be used to produce chimeric polypeptides (e.g., of Formula I or in Table 2) that may be used in diagnostic methods to detect infection by *E. chaffeensis* or *E. canis*, or may be used to induce an immune response in a subject (e.g., a human or a dog) against *E. chaffeensis* or *E. canis*.

An aspect of the present invention relates to an isolated polypeptide, wherein the isolated polypeptide comprises: (i) at least two of the immunogenic sequences of Table 1, or a sequence at least 90% identical (preferably at least 95% identical); and (ii) wherein at least one of the immunogenic sequences is contiguously repeated in the polypeptide. For example, in some embodiments, at least 2, 3, 4, 5, 6, or 7 immunogenic sequences are contiguously repeated in the isolated polypeptide. In some embodiments, each of the at least two immunogenic sequences of Table 1, or a sequence at least 90% identical are contiguously repeated 1, 2, 3, 4, 5, 6, or 7 times in the polypeptide. In some embodiments, the isolated polypeptide comprises one or more of (SEQ ID NOs:11-16 or 36-42), wherein the one or more of (SEQ ID NOs:11-16 or 36-42) are contiguously repeated 0, 1, 2, or 3 times. In some embodiments, each of the immunogenic sequences are contiguously repeated from 1 to 3 times in the polypeptide. In some embodiments, each of the immunogenic sequences are contiguously repeated from 1 to 2 times in the polypeptide. In some embodiments, the isolated polypeptide comprises at least 2, 3, 4, 5, 6, 7, 8, 9, 10, 11, or all of the following immunogenic sequences: TRP120 (SEQ ID NO:22), TRP140 (SEQ ID NO:23), A34N1 (SEQ ID NO:7), TRP63 (SEQ ID NO:18), TRP47 (SEQ ID NO:17), TRP75 (SEQ ID NO:19), TRP28 (SEQ ID NO:2), TRP36R1 (SEQ ID NO:3), TRP36R2 (SEQ ID NO:4), TRP36R3 (SEQ ID NO:6), TRP36CO (SEQ ID NO:36), TRP19 (SEQ ID NO:1), HSP (SEQ ID NO:24), or a sequence at least 90% identical (preferably at least 95% identical); wherein each of the immunogenic sequences are contiguously repeated from 1 to 7 times in the polypeptide. The isolated polypeptide may comprise TRP36R1 and TRP140. In some embodiments, the TRP36R1 is contiguously repeated 4-8 times, and wherein the TRP140 is contiguously repeated 1-3 times. The polypeptide may comprise or consists of 8 repeats of TRP36R1 and 4 repeats of TRP140. The polypeptide may comprise or consist of SEQ ID NO:27. The polypeptide may further comprise TRP19. The polypeptide may comprise or consist of SEQ ID NO:26. In some embodiments, the isolated polypeptide comprises at least two, at least three, at least four, at least five or all of the immunogenic sequences: TRP32, TRP120, TRP36R1, TRP140, TRP28, and/or HSP. In some embodiments, the TRP36R1 if present is repeated 2-6 times, and wherein the other immunogenic sequences are repeated 1-3 times. In some embodiments, the polypeptide comprises all of TRP32, TRP120, TRP36 (such as TRP36R1, TRP36R2, TRP36R3, and/or TRP36CO), TRP140, TRP28, and HSP. The polypeptide may comprise or consist of SEQ ID NO:28. In some embodiments, the polypeptide comprises TRP120, TRP36, TRP140, and TRP28. The polypeptide may comprise or consists of SEQ ID NO:29. In some embodiments, the isolated polypeptide comprises at least three, at least four, at least five or all of TRP32R1, TRP32R2, TRP32R3, TRP32R4, TRP120, and A34N1. In some embodiments, TRP120 and A34N1 are each contiguously repeated 1, 2, or 3 times. The polypeptide may comprise or consist of SEQ ID NO:25. The polypeptide may comprise at least two, at least three, or all of A34N1, TRP63, TRP47, and/or TRP75. The polypeptide may comprise A34N1 and TRP63. Each of the immunogenic sequences may be contiguously repeated 1-2 times. The polypeptide may comprise A34N1, TRP63, and TRP75. The polypeptide may comprise or consist of SEQ ID NO:34. In some embodiments, the polypeptide comprises A34N1, TRP63, and TRP47. The polypeptide may comprise or consist of SEQ ID NO:33. In some embodiments, the polypeptide comprises at least two, at least three, or all of A34N1, TRP63, TRP47, and/or TRP75. The polypeptide may comprise A34N1 and TRP63. In some embodiments, each of the immunogenic sequences are contiguously repeated 1-2 times. The polypeptide may comprise A34N1, TRP63, and TRP75. The polypeptide may comprise or consist of SEQ ID NO:34. The polypeptide may comprise A34N1, TRP63, and TRP47. The polypeptide may comprise or consist of SEQ ID NO:33. In some embodiments, the polypeptide comprises at least two, at least three, or all of TRP120, A34N1, TRP47, and/or TRP63. The polypeptide may comprise A34N1 and TRP120. Each of the immunogenic sequences may be contiguously repeated 1-2 times. The polypeptide may comprise A34N1, TRP120, and TRP63. The polypeptide may comprise or consist of SEQ ID NO:31. The polypeptide may comprise A34N1, TRP120, and TRP47. The polypeptide may comprise or consist of SEQ ID NO:32. The polypeptide may comprise A34N1, TRP120, TRP47, and TRP63. The polypeptide may comprise or consist of SEQ ID NO:30. In some embodiments, the polypeptide comprises at least two, at least three, or all of TRP36R1, TRP140, TRP95R, and/or TRP95C. Each of the immunogenic sequences may be contiguously repeated 1-2 times. The polypeptide may comprise TRP36R1, TRP140, TRP95R, and TRP95C. In some embodiments, the polypeptide comprises or consists of SEQ ID NO:35. The polypeptide may comprise or consist of a polypeptide of any one of (SEQ ID NOs: 25-35 or 43-44). The isolated polypeptide may comprise 3, 4, 5, 6, 7, 8, 9, or all of the following immunogenic sequences: TRP120, A34N1, TRP63, TRP47, TRP75, TRP28, TRP36 (such as TRP36R1, TRP36R2, TRP36R3, and/or TRP36CO), TRP19, TRP140, and/or HSP. In some embodiments, the polypeptide further comprises at least two of TRP36R1, TRP36R2, TRP36R3, and/or TRP36CO. The polypeptide may comprise TRP36R1, TRP36R2, and TRP36R3. The TRP36R1, TRP36R2, and TRP36R3 sequences may be separated by a linker. In some embodiments, the TRP36R1, TRP36R2, and TRP36R3 sequences are not separated by a linker. The polypeptide may comprise TRP36R1-R2-R3 (SEQ ID NO:11), TRP36R1-R3-R2 (SEQ ID NO:12), TRP36R2-R1-R3 (SEQ ID NO:13), TRP36R2-R3-R1 (SEQ ID NO:14), TRP36R3-R1-R2 (SEQ ID NO:15), or TRP36R3-R2-R1 (SEQ ID NO:16). In some embodiments, each of the immunogenic sequences in the polypeptide are contiguously repeated 1, 2, or 3 times. Each of the immunogenic sequences may be contiguously repeated 1 or 2 times. In some embodiments, the different immunogenic sequences are not separated by a linker or a spacer. In some embodiments, the different immunogenic sequences are separated by a linker or a spacer, such as for example a glycine linker. The glycine linker may have the amino acid sequence -$(G)_x$-, wherein X=3-5. In some embodiments, the polypeptide is less than 500, less than 450, less than 400, less than 350, less than 300, less than 250, less than 200, or less than 150 amino acids in length.

In some embodiments, the polypeptide is comprised in a pharmaceutical preparation. In some embodiments, the pharmaceutical preparation is formulated for parenteral, intravenous, subcutaneous, intranasal, sublingual, or intradermal administration. In some embodiments, the polypeptide is attached to a solid support (e.g., glass or plastic) or comprised in a diagnostic kit. In some embodiments, the solid support is comprised in a lateral flow assay, or microfluidic device.

Another aspect of the present invention relates to an isolated polypeptide of Formula I $(A_s\text{-}B_t\text{—}C_u\text{-}D_v\text{-}E_w\text{-}F_x\text{-}G_y\text{-}H_z)_n$, wherein A, B, C, D, E, F, G, and H is a peptide selected from SEQ ID NOs:1-24 and 36-42, or a sequence at least 90% identical (preferably at least 95% identical) to any one of (SEQ ID NOs:1-24 or 36-42), wherein s, t, u, v, x, y, and z is an integer 0-8, wherein at least two (e.g., 2, 3, 4, 5, 6, 7, or 8) of s-z are ≥1 and at least one (e.g., 1, 2, 3, 4, 5, 6, 7, or 8) of s-z is ≥2, and wherein n is an integer 1-5. In some embodiments, A is SEQ ID NO:8 (TRP36R1) and B is SEQ ID NO:23 (TRP140). In some embodiments, s is from 4 to 8, t is from 2 to 4, and n=1. In some embodiments, u, v, x, y, and z are zero. In some embodiments, wherein s=8 and t=4. The polypeptide may comprise or consist of SEQ ID NO:27. In some embodiments, at least two, three, four, five or six of s, t, u, v, x, y, and z are each 2-3; and wherein n=1. In some embodiments, A is TRP32 (e.g., TRP32R3 of SEQ ID NO:5), B is TRP120 (SEQ ID NO:22), C is TRP36R1 (SEQ ID NO:8), D is TRP140 (SEQ ID NO:23), E is TRP28 (SEQ ID NO:2), and F is HSP (SEQ ID NO:24). In some embodiments, z=0. The polypeptide may comprise or consist of SEQ ID NO:28. In some embodiments, the polypeptide is a polypeptide of Table 2 or any one of (SEQ ID NOs: 25-35 or 43-44).

Yet another aspect of the present invention relates to a pharmaceutical preparation comprising a polypeptide disclosed herein (e.g., of Formula I or in Table 2) or as described above, and a pharmaceutically acceptable excipient. The pharmaceutical preparation may be formulated for parenteral, intravenous, subcutaneous, intranasal, sublingual, or intradermal administration. The pharmaceutically acceptable excipient may comprise or consists of an adjuvant. In some embodiments, the adjuvant is an emulsion or liposomes, or wherein the adjuvant comprises a lipid. The emulsion may be an oil-in-water (O/W) emulsion or a water-in-oil (W/O) emulsion. In some embodiments, the adjuvant comprises a triterpenoid, a sterol, an immunomodulator, a polymer (e.g., diethyl-aminoethyl (DEAE)-dextran, polyethelyne glycol, or polyacrylic acid), and/or an immunostimulatory oligonucleotide (e.g., a CpG containing ODN). In some embodiments, the adjuvant comprises DEAE Dextran, an immunostimulatory oligonucleotide, and oil such as mineral oil, wherein the immunostimulatory oligonucleotide is a CpG containing ODN, and wherein the adjuvant formulation is a water-in-oil (W/O) emulsion. In some embodiments, the adjuvant comprises a saponin, a sterol, a quaternary ammonium compound, a polymer, and an ORN/ODN. In some embodiments, the saponin is Quil A or a purified faction thereof, the sterol is cholesterol, the quaternary ammonium compound is dimethyl dioctadecyl ammonium bromide (DDA), the polymer is polyacrylic acid, and the ORN/ODN is a CpG. In some embodiments, the saponin is present in an amount of about 1 µg to about 5,000 µg per dose, the sterol is present in an amount of about 1 µg to about 5,000 µg per dose, the quaternary ammonium compound is present in an amount of about 1 µg to about 5,000 µg per dose, and the polymer is present in an amount of about 0.0001% v/v to about 75% v/v. In some embodiments, the adjuvant further comprises a glycolipid such as, e.g., N-(2-deoxy-2-L-leucylamino-β-D-glucopyranosyl)-N-octadecyldodecanamide acetate. In some embodiments, the adjuvant comprises a triterpenoid saponin, a sterol, a quaternary ammonium compound, and a polyacrylic acid polymer. In some embodiments, the saponin is Quil A or a purified fraction thereof, the sterol is cholesterol, and the quaternary ammonium compound is dimethyl dioctadecyl ammonium bromide (DDA). In some embodiments, the saponin is present in an amount of about 1 mg to about 5,000 mg per dose, the sterol is present in an amount of about 1 mg to about 5,000 mg per dose, the quaternary ammonium compound is present in an amount of about 1 mg to about 5,000 mg per dose, and the polyacrylic acid polymer is present in an amount of about 0.0001% v/v to about 75% v/v. The adjuvant may comprise a water-in-oil emulsion. The water-in-oil emulsion may comprise an oily phase and an aqueous phase, a polycationic carrier (e.g., DEAE dextran), and a CpG containing immunostimulatory oligonucleotide. In some embodiments, the composition further comprises an aluminum hydroxide gel. In some embodiments, the polycationic carrier is DEAE dextran. The composition may comprise an emulsion or an oil-in-water (O/W) emulsion. In some embodiments, the emulsion comprises an aqueous phase that comprises an alkyl-polyacrylic acid (alkyl-PAA) or both an acrylic polymer and dimethyl dioctadecyl ammonium bromide (DDA). In some embodiments, the aqueous phase of the oil-in-water emulsion comprises dimethyl dioctadecyl ammonium bromide (DDA) and an alkyl-polyacrylic acid (alkyl-PAA). In some embodiments, the alkyl-PAA is decyl-PAA, octyl-PAA, butyl-PAA, or methyl-PA. In some embodiments, the acrylic polymer is a polymer of acrylic acid crosslinked with polyallyl sucrose. The composition may comprise a water-in-oil (W/O) emulsion comprising a non-mineral oil and an emulsifier (e.g., a mannide mono-oleate emulsifier). In some embodiments, the adjuvant is MF59, AS01, AS02, AS03, AS04, Virosomes, CAF01, CAF04, CAF05, an acrylic polymer/DDA emulsion, a CpG/DEAE emulsion, a saponin/cholesterol/ DDA adjuvant, or a polyacrylic acid polymer emulsion. In some embodiments, the composition further comprises an *Ehrlichia* bacterin. The bacterin can be, e.g., a heat-inactivated *E. canis*, a chemically-inactivated *E. canis*, a heat-inactivated *E. chaffeensis* or a chemically-inactivated *E. chaffeensis*. In some embodiments, the bacterin is a chemically-inactivated bacterin that has been inactivated with formaldehyde, formalin, bi-ethylene amine, radiation, ultraviolet light, beta-propiolactone treatment, or formaldehyde.

Another aspect of the present invention relates to a nucleic acid encoding a polypeptide provided herein (e.g., a polypeptide of Formula 1 or in Table 2) or as described above. The nucleic acid may be a DNA segment. The nucleic acid may be comprised in an expression vector.

Yet another aspect of the present invention relates to a host cell comprising a nucleic acid provided herein (e.g., a polypeptide of Formula 1 or in Table 2) or as described above. In some embodiments, the cell expresses the nucleic acid.

Another aspect of the present invention relates to a method of detecting antibodies that specifically bind an *Ehrlichia* organism in a test sample, comprising: (a) contacting an isolated polypeptide provided herein (e.g., a polypeptide of Formula 1 or in Table 2) or as described above; (b) detecting the peptide-antibody complexes; wherein the detection of the peptide-antibody complexes is an indication that antibodies specific for an *Ehrlichia* organism are present in the test sample, and wherein the absence of the peptide-antibody complexes is an indication that antibodies specific an *Ehrlichia* organism are not present in the test sample. The *Ehrlichia* organism may be an *Ehrlichia chaffeensis* organism or an *Ehrlichia canis* organism. The step of detecting may comprise performing an enzyme-linked immunoassay, a radioimmunoassay, an immunoprecipitation, a fluorescence immunoassay, a chemiluminescent assay, an immunoblot assay, a lateral flow assay, a flow cytometry assay, a multiplex immunoassay, a mass spectrometry assay, or a particulate-based assay. The step of detecting may comprise a lateral flow assay or an enzyme-linked immunoassay, wherein the enzyme-linked immunoassay is an ELISA.

Yet another aspect of the present invention relates to a method of identifying an *Ehrlichia* infection in a mammalian subject comprising: (a) contacting a biological sample from the subject with an isolated polypeptide provided herein (e.g., a polypeptide of Formula 1 or in Table 2) or as described above under conditions that allow peptide-antibody complexes to form; and (b) detecting the peptide-antibody complexes; wherein the detection of the peptide-antibody complexes is an indication that the subject has an *Ehrlichia* infection. The step of detecting may comprise performing an enzyme-linked immunoassay, a radioimmunoassay, an immunoprecipitation, a fluorescence immunoassay, a chemiluminescent assay, an immunoblot assay, a lateral flow assay, a flow cytometry assay, a multiplex immunoassay, a dipstick test, or a particulate-based assay. In some embodiments, the subject is a human or a dog.

Another aspect of the present invention relates to a kit comprising: (a) an isolated polypeptide disclosed herein or as described above (e.g., a polypeptide of Formula 1 or in Table 2), (b) an anti-dog or anti-human secondary antibody linked to a reporter molecule; and, (c) an appropriate reagent for detection of the reporter molecule. The peptide may be immobilized on a membrane or a microtiter plate. The reporter molecule may be selected from the group consisting of luciferase, horseradish peroxidase, a luminous nanoparticle, P-galactosidase, and a fluorescent label. The luminous nanoparticle may be a strontium aluminate nanoparticle. The kit may further comprise a dilution buffer for dog or human serum. The kit may comprise a lateral flow immunoassay or a lateral flow immunochromatographic assay. In some embodiments, the kit comprises an enzyme-linked immunosorbent assay (ELISA).

Yet another aspect of the present invention relates to a method of inducing an immune response in a mammalian subject comprising administering to the subject an effective amount of a pharmaceutical preparation comprising a polypeptide provided herein (e.g., a polypeptide of Formula 1 or in Table 2) or a pharmaceutical preparation as described above. The subject may be a human or a dog. The pharmaceutical preparation may be administered subcutaneously, intramuscularly, nasally, via inhalation or aerosol delivery, or intradermally.

Another aspect of the present invention relates to a method of treating an *Ehrlichia chaffeensis* or *Ehrlichia canis* infection in a subject comprising: (a) contacting a biological sample from the subject with an isolated polypeptide provided herein provided herein (e.g., a polypeptide of Formula 1 or in Table 2) or as described above under conditions that allow peptide-antibody complexes to form; (b) detecting the peptide-antibody complexes; wherein the detection of the peptide-antibody complexes is an indication that the subject has an *Ehrlichia chaffeensis* or *Ehrlichia canis* infection; and (c) administering a therapeutic compound to treat *Ehrlichia* infection in the subject. The step of detecting may comprise performing an enzyme-linked immunoassay, a radioimmunoassay, an immunoprecipitation, a fluorescence immunoassay, a chemiluminescent assay, an immunoblot assay, a lateral flow assay, a flow cytometry assay, a multiplex immunoassay, a dipstick test, or a particulate-based assay. The subject may be a dog or a human. The therapeutic compound may be an antibiotic (e.g., doxycycline).

As used herein, the term "contiguously repeated", when used to describe a nucleic acid sequence or amino acid sequence, indicates that the sequence is repeated in a polypeptide from an N-terminus to C-terminus direction. For example, for amino acid sequence —$X_1$—, if the sequence is repeated zero times, then it is included in the polypeptide without repetition as —$X_1$—. If the sequence —$X_1$— is contiguously repeated once, then the polypeptide contains —$X_1$—$X_1$—. If the sequence —$X_1$— is contiguously repeated twice then the polypeptide contains —$X_1$—$X_1$—$X_1$—. The number of contiguous repetitions of the sequence —$X_1$— may be described by the formula —$(X_1)_{(n+1)}$—, wherein (n+1) refers to the number of contiguous repetitions. Preferably, the contiguously repeated sequences are repeated without any linker or spacer sequence separating the contiguously repeated sequences. Nonetheless, in some embodiments, a spacer or linker (e.g., a glycine linker such as -G-, -GG-, or -GGG-) may be used to separate the contiguously repeated sequences. In some preferred embodiments, different contiguously repeated sequences are separated by a spacer or linker (e.g., a glycine linker such as -G-, -GG-, or -GGG-); for example, in sequence —$X_1$—$X_1$-GG-$X_2$—$X_2$—$X_2$—, sequence —$X_1$— is contiguously repeated once and sequence —$X_2$— is contiguously repeated twice, wherein the different contiguously repeated sequences are separated by the glycine linker -GG-.

As used herein, the term "polypeptide" encompasses amino acid chains comprising at least 50 amino acid residues, and more preferably at least 100 amino acid residues, wherein the amino acid residues are linked by covalent peptide bonds. As used herein, an "antigenic polypeptide" or an "immunoreactive polypeptide" is a polypeptide which, when introduced into a vertebrate, can stimulate the production of antibodies in the vertebrate, i.e., is antigenic, and wherein the antibody can selectively recognize and/or bind the antigenic polypeptide. An antigenic polypeptide may comprise or consist of an immunoreactive sequence(s) derived from an immunoreactive *Ehrlichia* protein as described herein; for example, polypeptides in Table 1, Table 2, and Formula I), and the polypeptide may comprise one or more additional sequences. In some embodiments, the additional sequences may be derived from a native *Ehrlichia* antigen and may be heterologous, and such sequences may (but need not) be immunogenic. In some embodiments, the antigenic polypeptide or immunoreactive polypeptide may be covalently bound to a solid substrate, e.g., in an immunoassay such as a lateral flow test, etc.

*Ehrlichia* immunoreactive polypeptides as described herein (e.g., in Table 2 or Formula I) may be a recombinant polypeptide, synthetic polypeptide, purified polypeptide, immobilized polypeptide, detectably labeled polypeptide, encapsulated polypeptide, or a vector-expressed polypeptide. In various embodiments, the *Ehrlichia* immunoreactive polypeptides provided herein may be truncated or may comprise a deletion mutation, without eliminating the immunoreactivity of the resulting peptide or polypeptide. An immunoreactive peptide or polypeptide disclosed herein may also be comprised in a pharmaceutical composition such as, e.g., a vaccine composition that is formulated for administration to a human or canine subject.

"Bacterin" as used herein refers to one or more killed bacteria which may be used as a component of a vaccine or immunogenic composition. The bacterin may be comprised in a suspension. In some preferred embodiments, the bacterin is a heat-inactivated *Ehrlichia* (e.g., a heat-inactivated *E. Canis*) or a chemically-inactivated *Ehrlichia* (e.g., a chemically-inactivated *E. Canis*).

"Adjuvant" as used herein refers to any substance that increases the humoral or cellular immune response to an antigen. In some embodiments, Adjuvants be used to both allow for the controlled release of antigens from the injection site of a vaccine and stimulate the immune system of the subject receiving the vaccine composition.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation or error of the device used determine the value, the method employed to determine the value, or the variation that exists among the study subjects or samples.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1: Purification and Characterization of *E. chaffeensis* chimera TRP32/TRP120/A34 (Combined=SEQ ID NO: 25). TRP32R1=SEQ ID NO: 3; TRP32R2=SEQ ID NO: 4; TRP32R3=SEQ ID NO: 5; TRP32R4=SEQ ID NO: 6; TRP120=SEQ ID NO: 22; A34N1=SEQ ID NO: 7.

FIG. 2: Purification and Characterization of *E. chaffeensis* chimera TRP140/TRP36/TRP19 (Combined=SEQ ID NO: 26). TRP19=SEQ ID NO: 1; TRP36=SEQ ID NO: 8; TRP140=SEQ ID NO: 23.

FIG. 3: Purification and Characterization of *E. canis* chimera TRP36/TRP140 (Combined=SEQ ID NO: 27). TRP36=SEQ ID NO: 8; TRP140=SEQ ID NO: 23.

FIG. 4: Purification and Characterization of *E. chaffeensis* and *E. canis* chimera TRP32/TRP120/TRP36/TRP140/HSP (Combined=SEQ ID NO: 28). TRP32=SEQ ID NO: 5; TRP120=SEQ ID NO: 22; TRP36=SEQ ID NO: 8; TRP140=SEQ ID NO: 23; P28=SEQ ID NO: 2; HSP=SEQ ID NO: 24.

FIG. 5: Purification and Characterization of *E. chaffeensis* and *E. canis* chimera TRP120/TRP140/TRP36/TRP28 (Combined=SEQ ID NO: 29). TRP120=SEQ ID NO: 22; TRP140=SEQ ID NO: 23; TRP36=SEQ ID NO: 8; P28=SEQ ID NO: 2.

FIG. 6: Additional *Ehrlichia* chimeric polypeptides.

DESCRIPTION OF ILLUSTRATIVE EMBODIMENTS

In some embodiments, an immunoreactive polypeptide (e.g., a polypeptide of Formula I or a polypeptide in Table 2) described herein may be used as diagnostic or prophylactic tools for detection of or immunization against *Ehrlichia* infection. In particular embodiments, immunoreactive polypeptides disclosed herein may be useful in solution-phase assays, or in assays in which the isolated immunoreactive polypeptide is immobilized on a surface of a support substrate. Alternatively, an immunoreactive polypeptide described herein may be comprised in a vaccine formulation to induce a protective immune response or an immune response against *E. chaffeensis* in a subject. One or more immunoreactive polypeptides as described herein may be immobilized on a surface by covalent attachment, encapsulation, or adsorption using methods generally known in the art, and may include the use of cross-linkers, capture molecules and such like, to which peptides may be coupled, conjugated, or cross-linked.

I. CHIMERIC POLYPEPTIDES

As described in the foregoing summary, certain aspects of the present disclosure concern chimeric *Ehrlichia* polypeptides, such as polypeptides comprising or consisting of at least two of the peptides of Table 1 or a polypeptide of Table 2. The chimeric polypeptides may be produced to comprise at least two of the peptides of Table 1 which can be continuously repeated (e.g., from 2 to 8, preferably 2 to 6, or even more preferably 2 to 4 times) in the polypeptide. The chimeric polypeptide can comprise 3, 4, 5 or more of the above immunogenic peptides. Each of the immunogenic peptides may be repeated 0, 1, 2, 3, 4, 5, 6, 7, or 8 times in the chimeric polypeptide. Exemplary configurations include, but are not limited to, 2×2, 2×2×2, 2×2×2×2, 3×2, 2×3, 3×2×2, 2×3×2, 2×2×3, 3×2×2×2, 2×3×2×2, 2×2×3×2, 2×2×2×3, 3×3, 3×3×3, 3×3×2, 2×2×3, 3×3×3×3, 3×3×3×6, and 2×2×4×2×2×2.

TABLE 1

Ehrlichia immunogenic peptides.

| Immunogenic Peptide | Sequence | | Species |
|---|---|---|---|
| TRP19 | HFTGPTSFEVNLSEEEKMELQEVS | SEQ ID NO: 1 | *E. canis* |
| P28 | AKEEKNATAKTFQLKGDWDGA | SEQ ID NO: 2 | *E. canis* |
| TRP32R1 | SDLHESSFVELPGPSKEEVQFEDDAKNVVY | SEQ ID NO: 3 | *E. chaffeensis* |
| TRP32R2 | SDLHGSFSVELFDPSKEEVQLESDLQQSSN | SEQ ID NO: 4 | *E. chaffeensis* |
| TRP32R3 | SDLHGSFSVELFDPFKEAVQLGNDLQQSSD | SEQ ID NO: 5 | *E. chaffeensis* |
| TRP32R4 | SDSHEPSHLELPSLSEEVIQLESDLQQSSN | SEQ ID NO: 6 | *E. chaffeensis* |
| A34N1 | VRSITDPRIVVQQEADQQQEVQQQAD | SEQ ID NO: 7 | *E. chaffeensis* |

TABLE 1-continued

Ehrlichia immunogenic peptides.

| Immunogenic Peptide | Sequence | | Species |
|---|---|---|---|
| TRP36R1 | TEDSVSAPA | SEQ ID NO: 8 | E. canis |
| TRP36R2 | ASVVPEAE | SEQ ID NO: 9 | E. canis |
| TRP36R3 | TEDPVSATA | SEQ ID NO: 10 | E. canis |
| TRP36R1-R2-R3 | TEDSVSAPA ASVVPEAE TEDPVSATA | SEQ ID NO: 11 | |
| TRP36R1-R3-R2 | TEDSVSAPA TEDPVSATA ASVVPEAE | SEQ ID NO: 12 | |
| TRP36R2-R1-R3 | ASVVPEAE TEDSVSAPA TEDPVSATA | SEQ ID NO: 13 | |
| TRP36R2-R3-R1 | ASVVPEAE TEDPVSATA TEDSVSAPA | SEQ ID NO: 14 | |
| TRP36R3-R1-R2 | TEDPVSATA TEDSVSAPA ASVVPEAE | SEQ ID NO: 15 | |
| TRP36R3-R2-R1 | TEDPVSATA ASVVPEAE TEDSVSAPA | SEQ ID NO: 16 | |
| TRP47 | ASVSEGDAVVNAVSQETPA | SEQ ID NO: 17 | E. chaffeensis |
| TRP63 | SLFTEEEKILAILSARFICK | SEQ ID NO: 18 | E. chaffeensis |
| TRP75 | DVKDNKPSDVKLPVIKAE | SEQ ID NO: 19 | E. chaffeensis |
| TRP95R | DDSKLPVIKVEDKSKLQDTKDKKR | SEQ ID NO: 20 | E. canis |
| TRP95C | KKIKEYDEDYTITYYYDDD | SEQ ID NO: 21 | E. canis |
| TRP120 | SKVEQEETNPEVLIKDLQDVAS | SEQ ID NO: 22 | E. chaffeensis |
| TRP140 | EHSSSEVGEKVSETSKEENTPEVKA | SEQ ID NO: 23 | E. canis |
| HSP | YGAPEITKDGYKVIKSIKPED | SEQ ID NO: 24 | E. chaffeensis |
| TRP36CO | EASVVPAAEAPQPAQQTEDEFFSDGIEA | SEQ ID NO: 36 | E. canis |
| TRP36CO-R1 | EASVVPAAEAPQPAQQTEDEFFSDGIEA TEDSVSAPA | SEQ ID NO: 37 | |
| TRP36R1-CO | TEDSVSAPA EASVVPAAEAPQPAQQTEDEFFSDGIEA | SEQ ID NO: 38 | |
| TRP36CO-R3 | EASVVPAAEAPQPAQQTEDEFFSDGIEA TEDPVSATA | SEQ ID NO: 39 | |
| TRP36R3-CO | TEDPVSATA EASVVPAAEAPQPAQQTEDEFFSDGIEA | SEQ ID NO: 40 | |
| TRP36R1-R3 | TEDSVSAPA TEDPVSATA | SEQ ID NO: 41 | |
| TRP36R3-R1 | TEDPVSATA TEDSVSAPA | SEQ ID NO: 42 | |

In some embodiments, it is anticipated that TRP36R1, TRP36R2, and TRP36R3 may be switched within a chimeric polypeptide. For example, in some embodiments, a TRP36R1 sequence in a chimeric polypeptide may be switched for TRP36R2 or TRP36R3. In some embodiments, a TRP36R1, TRP36R2, or TRP36R3 sequence in a chimeric polypeptide may be switched for TRP36CO. In some embodiments, it has been observed that TRP36R1, TRP36R2, TRP36R3, and/or TRP36CO may be contiguously located in a chimeric polypeptide, e.g., as shown in SEQ ID NOs:11-16 and 38-43. In some embodiments, 2, 3, or all of TRP36R1, TRP36R2, TRP36R3, and/or TRP36CO may be contiguously located in a chimeric polypeptide. Similarly, it is anticipated that, in some embodiments, TRP32R1, TRP32R2, TRP32R3, and TRP32R4 may be switched within a chimeric polypeptide. In some embodiments, 2, 3, or all of TRP32R1, TRP32R2, TRP32R3, and/or TRP32R4 may be contiguously located in a chimeric polypeptide (e.g., wherein the polypeptide contains -TRP32R1-TRP32R2-TRP32R3- or -TRP32R1-TRP32R2-TRP32R3-TRP32R4-, etc.).

The chimeric polypeptides may be produced to comprise at least two of the above peptides which can be continuously repeated (e.g., once, from 2 to 8, preferably 2 to 6, or even more preferably 2 to 4, times) in the polypeptide. The chimeric polypeptide can comprise 3, 4, 5 or more of the above immunogenic peptides from Table 1. Each of the immunogenic peptides may be repeated 1, 2, 3, 4, 5, 6, 7, or 8 times in the chimeric polypeptide. The peptides within the polypeptide construct may be separated by a linker. The linker can be a poly-glycine linker (e.g., GG, GGG, GGGG, or GGGGG). The polypeptide constructs may comprise a heat shock protein (HSP) sequence (SEQ ID NO:24). Constructs were produced from the above immunogenic peptides as listed below (e.g., Table 2) and exemplary chimeric polypeptides are depicted in FIGS. 1-5.

In some embodiments, the chimeric polypeptide may comprise at least two or three immunogenic peptide isoforms. For example, the polypeptide may be produced by linking TRP36R1, TRP36R2, TRP36R3, and/or TRP36CO in various configurations as listed in Table 1 including TRP36R1-R2-R3, TRP36R1-R3-R2, TRP36R2-R1-R3, TRP36R2-R3-R1, TRP36R3-R1-R2, TRP36R3-R2-R1, TRP36CO-R1, TRP36R1-CO, TRP36CO-R3, TRP36R3-CO, TRP36R1-R3, and TRP36R3-R1. The polypeptide may be produced by linking TRP95R and TRP95C as TRP95R-C or TRP95C-R. In some embodiments, the polypeptide may be produced by linking TRP32R1, TRP32R1, TRP32R3, and/or TRP32R4 in various configurations.

In some embodiments, the chimeric construct may have a sequence as described by Formula I, below:

$$(A_s\text{-}B_t\text{—}C_u\text{-}D_v\text{-}E_w\text{-}F_x\text{-}G_y\text{-}H_z)_n,$$  Formula I:

wherein A-H comprise a peptide selected from SEQ ID NOs:1-24 and 36-42, s-z is an integer 0-8, wherein at least two of s-z are ≥1 and at least one of s-z is ≥2, and n is an integer 1-5. Peptides A-H may be each be independently selected from SEQ ID NOs:1-24 and 36-42. Preferably, the chimeric construct may have a sequence of Formula I, wherein at least two of s-z are ≥2. The chimeric construct may comprise a linker or spacer to separate the peptides A-H of Formula I.

Exemplary derivatives of Formula I may comprise, but are not limited to:

$A_2\text{-}B_2\text{—}C_2$;
$A_1\text{-}B_3\text{—}C_3$;
$A_3\text{-}B_3\text{—}C_3$;
$A_2\text{-}B_2\text{—}C_2\text{-}D_2$;
$A_3\text{-}B_2\text{—}C_2\text{-}D_2$;
$A_3\text{-}B_3\text{—}C_6\text{-}D_3$;
$(A_1\text{-}B_2\text{—}C_1)_3$;
$A_8\text{-}B_4$; and
$A_2\text{-}B_2\text{—}C_4\text{-}D_2\text{-}E_2\text{-}F_2$.

In some embodiments, the polypeptide of Formula I comprises or consists of any one of SEQ ID NOs: 11-16 or 38-42. In some embodiments, the polypeptide of Formula I comprises or consists of a polypeptide of Table 2.

TABLE 2

Chimeric Ehrlichia Polypeptides

| Construct | Sequence | Species |
|---|---|---|
| TRP32/TRP120/A34N1 (32R1/32R2/32R3/32R4/3 x 120/3 x 43) | SEQ ID NO: 25 | E. chaffeensis |
| TRP140/TRP36/TRP19 (19/2 x 36/140) x 3 | SEQ ID NO: 26 | E. canis |
| TRP36/TRP140 (8 x 36/4 x 140) | SEQ ID NO: 27 | E. canis |
| TRP32/TRP120/TRP36/TRP140/TRP28/HSP (2 x 32/2 x 120/4 x 36/ 2 x 140/2 x 28/2 x HSP) | SEQ ID NO: 28 | E. chaffeensis and E. canis |
| TRP120/TRP140/TRP36/TRP28 (3 x 120/3 x 140/6 x 36/3 x 28) | SEQ ID NO: 29 | E. chaffeensis and E. canis |
| TRP120/A34N1/TRP63/TRP47 (2 x 120/2 x 34/2 x 63/2 x 47) | SEQ ID NO: 30 | E. chaffeensis |
| TRP120/A34N1/TRP63 (2 x 120/2 x 34/2 x 63) | SEQ ID NO: 31 | E. chaffeensis |
| TRP120/A34N1/TRP47 (2 x 120/2 x 34/2 x 63/2 x 47) | SEQ ID NO: 32 | E. chaffeensis |

TABLE 2-continued

Chimeric Ehrlichia Polypeptides

| Construct | Sequence | Species |
|---|---|---|
| A34N1/TRP63/TRP47<br>(2 × 34/2 × 63/2 × 47) | SEQ ID NO: 33 | E. chaffeensis |
| A34N1/TRP63/TRP75<br>(2 × 34/2 × 63/2 × 75) | SEQ ID NO: 34 | E. chaffeensis |
| TRP36/TRP140/TRP95R/TRP95C<br>(2 × 36/2 × 140/2 × 95R/2 × 95C) | SEQ ID NO: 35 | E. canis |
| TRP36R1/TRP36R2/TRP36CO<br>(2 × 36/2 × 36/2 × 36) | SEQ ID NO: 43 | E. canis |
| TRP36R1/TRP36R2<br>(2 × 36/2 × 36) | SEQ ID NO: 44 | E. canis |

In some embodiments, it is anticipated that a polypeptide having at least 90%, more preferably at least 95%, 97.5%, or at least 99% sequence identity to a polypeptide of Table 2 or a polypeptide of Formula I, that retains at least some of its immunoreactivity may be used in various embodiments as described herein (e.g., in a diagnostic test, or to induce an immune response against Ehrlichia in a subject, for inclusion in a vaccine composition). In some embodiments, the polypeptide may be used to generate an antibody that selectively binds the protein, and the antibody may be used, e.g., in a diagnostic assay; for example, in some embodiments, the antibody is labelled or attached to a solid substrate (e.g., in a lateral-flow test).

In some aspects, a contiguous repeat of a specific peptide may comprise two or more isoforms of the immunogenic peptide. For example, a contiguous repeat may comprise TRP32R1, TRP32R2, TRP32R3, and/or TRP32R4. Another contiguous repeat can comprise TRP95C and TRP95R or different isoforms of TRP36 including TRP36R1, TRP36R2, TRP36R3, and/or TRP36CO. Thus, the same or different isoforms of the protein may thus be contiguously repeated in some embodiments without separation by a spacer or glycine spacer.

A variety of linkers or spacers can be used in chimeric Ehrlichia polypeptides of the embodiments. In some embodiments, a linker or spacer can be a random string of one or more amino acids (e.g., 2, 3, 4, 5, 10, 15, or 20 amino acids). In other embodiments, the linker has a particular sequence. For example, in some embodiments, the linker or spacer can be a poly-glycine linker (e.g., GG, GGG, or GGGG; also referred to as a glycine linker herein). Other linkers or spacers that may be used in various embodiments include, e.g., the 218 (GSTSGSGKPGSGEGSTKG; SEQ ID NO: 45), the HL (EAAAK; SEQ ID NO: 46), and the $G_4S$ (GGGGS; SEQ ID NO: 47) linkers. In some preferred embodiments, groups of different contiguously repeated sequences are separated in a polypeptide by a linker or spacer such as, e.g., a glycine linker (e.g., —$X_1$—$X_1$—$X_1$-GGG-$X_2$—$X_2$— shows amino sequence —$X_1$— contiguously repeated twice, amino acid sequence —$X_2$— is contiguously repeated once, and the different contiguously repeated sequences are separated by the poly-glycine linker -GGG-).

In some embodiments, an immunoreactive polypeptide provided herein (e.g., derived from two or more peptides in Table 1 or a polypeptide in Table 2) may be immobilized onto a surface of a support or a solid substrate; for example, the immunoreactive polypeptide may be immobilized directly or indirectly by coupling, cross-linking, adsorption, encapsulation, or by any appropriate method known in the art. By way of non-limiting example, binding of an immunoreactive polypeptide disclosed herein by adsorption to a well in a microtiter plate or to a membrane may be achieved by contacting the peptide, in a suitable buffer, with the well surface for a suitable amount of time. The contact time can vary with temperature, but is typically between about 1 hour and 1 day when using an amount of peptide ranging from about 50 ng to about 1 mg, and preferably about 250-700 ng or about 450-550 ng.

In some embodiments, an immunoreactive polypeptide disclosed herein is covalently attached to a support substrate by first reacting the support with a reagent that will chemically react with both the support and a functional group (i.e., crosslink), such as a hydroxyl or amino group, on the peptide. For example, an immunoreactive polypeptide may be crosslinked to a surface through an amine or carboxylic group on either end of the peptide, and a peptide may be crosslinked through a group on each end of the polypeptide (i.e., head-to-tail crosslinked). Such peptomers (i.e., head-to-tail crosslinked or otherwise immobilized peptides) may be used with both diagnostic and therapeutic methods of the present disclosure.

In some embodiments, an isolated polypeptide comprising a sequence of a polypeptide of Formula I or a polypeptide Table 2, wherein the isolated peptide or polypeptide is immobilized on a surface of a support substrate. In some embodiments, the polypeptide is selected from the group consisting of Table 2. Numerous support substrates for peptide immobilization are known in the art which may be employed with an immunoreactive polypeptide disclosed herein, formed from materials such as, for example, latex, polystyrene, nylon, nitrocellulose, cellulose, silica, agarose, inorganic polymers, lipids, proteins, sugars, or magnetic resin. A person of ordinary skill in the art may select the support substrate that is appropriate for a given application. In particular embodiments, a support substrate may be a reaction chamber, a microplate well, a membrane, a filter, a paper, an emulsion, a bead, a microbead, a microsphere, a nanocrystal, a nanosphere, a dipstick, a card, a glass slide, a microslide, a lateral flow apparatus, a microchip, a comb, a silica particle, a magnetic particle, a nanoparticle, or a self-assembling monolayer.

II. DETECTABLY-LABELED IMMUNOREACTIVE POLYPEPTIDES

An immunoreactive polypeptide (e.g., comprising two or more peptide of Table 1, or a polypeptide of Table 2) may be conjugated to or attached to detectable label such as, for example, a radioactive isotope, a non-radioactive isotope, a particulate label, a fluorescent label, a chemiluminescent label, a paramagnetic label, an enzyme label or a colorimetric label. The detectably-labelled polypeptide may be used, e.g., in diagnostic or prophylactic methods and compositions. In certain embodiments, the polypeptide portion of the detectably labeled immunoreactive polypeptide may be immobilized on a surface of a support substrate. In other embodiments, the detectable label may be used to immobilize the detectably labeled immunoreactive peptide to the surface of a support substrate.

As used herein, "detectable label" is a compound and/or element that can be detected due to its specific functional properties, and/or chemical characteristics, the use of which allows the peptide to which it is attached be detected, and/or further quantified if desired.

In some embodiments, the probe is a photoluminescent probe, such as a fluorophore or a nanoparticle, such as for example a strontium aluminate nanoparticle (e.g., see Paterson et al., 2014). Exemplary labels include, but are not limited to, a particulate label such as colloidal gold, a radioactive isotope such as astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{51}$iron, $^{32}$phosphorus, rhenium186, rhenium188, $^{75}$selenium, $^{35}$sulphur, technicium-99, technetium-99m or yttrium$^{90}$, a colorimetric label such as dinitrobenzene, dansyl chloride, dabsyl chloride, any of the azo, cyanin or triazine dyes, or chromophores disclosed in U.S. Pat. Nos. 5,470,932, 5,543,504, or 6,372,445, all of which are incorporated herein by reference; a paramagnetic label such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III), a fluorescent label such as Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red, or *Lucifer* Yellow, an enzyme label such as urease, luciferase, alkaline phosphatase, (horseradish) hydrogen peroxidase, or glucose oxidase, or a chemiluminescent label such as luminol, phthalazinedione, and others disclosed in any of U.S. Pat. Nos. 4,373,932, 4,220,450, 5,470,723, and U.S. Patent Application 2007/0264664, all of which are incorporated herein by reference.

III. METHODS OF PRODUCING AN IMMUNOREACTIVE POLYPEPTIDE

An immunoreactive polypeptide as described herein may be produced using in vitro transcription and translation (IVTT) methods, may be recombinantly produced using a variety of cell types (e.g., bacterial cells, mammalian cells, *E. coli*, yeast, and insect cells, etc.), or in some instances may be synthesized (e.g., using solid-phase synthesis). In some embodiments, IVTT and synthetic methods can provide certain advantages over recombinant approaches, since the resulting polypeptides can produced highly pure forms without contaminating bacterial or other proteins that might result in false positive reactions when utilizing recombinant proteins. Thus, IVTT and synthetic methods have an advantage of lacking many of the costly and laborious purification procedures often associated with recombinant methodologies.

A variety of IVTT approaches are known in the art and may be used in various embodiments. IVTT generally involves cell-free methods for production or synthesis of a protein from DNA. The cell-free system for protein production may use, e.g., *E. coli* extract, protozoan extracts, yeast extracts, human cell extract, wheat germ extract, mammalian extracts, extracts from cultured human cell lines, rabbit reticulocyte lysate, insect cell extract, or reconstituted and purified *E. coli* components. A variety of kits are commercially available including, e.g., RTS (FivePrime, San Francisco, Calif.), Expressway™ (Life Technologies); S30 T7 high yield (Promega), One-step human IVT (Thermo Scientific), WEPRO® (CellFree Sciences), TNT® coupled (Promega), RTS CECF (5 PRIME), TNT® Coupled (Promega), Retic lysate IVT™ (Life Technologies); TNT® T7 (Promega), EasyXpress Insect kit(Qiagen/RiN A), PURExpress® (New England Biolabs), and PURESYSTEM® (BioComber). Such methods can be used to incorporate unnatural amino acids into proteins, if desired. Cell-free expression systems that may be used in various embodiments are also described, e.g., in Zemella et al., 2015.

An isolated immunoreactive protein as disclosed herein may be produced in some embodiments using an appropriate method known in the organic chemistry arts. For example, peptides may be produced using one of the established solid-phase peptide synthesis techniques that are well known in the art. In some embodiments, peptides may be synthesized using equipment for automated peptide synthesis that is widely available from commercial suppliers such as Perkin Elmer (Foster City, Calif.), or the peptide may be chemically synthesized using solution-phase techniques such as those described in Carpino et al., 2003 or U.S. Patent Application 2009/0005535. In some embodiments, the peptides or shorter proteins may be synthesized, e.g., using solid-phase peptide synthesis (SPPS), t-Boc solid-phase peptide synthesis, or Fmoc solid-phase peptide synthesis.

In some embodiments, an immunoreactive protein as described herein can be recombinantly prepared from a nucleic acid encoding the peptide. Such a nucleic acid may be operably linked to an expression vector. By way of nonlimiting example, an immunoreactive protein may be expressed from a vector and isolated from the growth media of a host cell comprising the vector. In some embodiments, the immunoreactive protein may be produced in a cell-free system from a nucleic acid encoding the peptide.

An immobilized immunoreactive protein as disclosed herein may be conjugated, crosslinked, or adsorbed, either directly or indirectly onto a surface of a support substrate. In some embodiments, an immobilized immunoreactive protein or peptide may be synthesized onto a support substrate.

It is anticipated that virtually any method of protein or peptide immobilization known in the art which would not impact the structure or function of the disclosed peptides may be used to immobilize an immunoreactive protein or peptide as disclosed herein. For example, peptide immobilization may be accomplished using a crosslinking or conjugation agent such as methyl-p-hydroxybenzimidate, N-succinimidyl-3-(4-hydroxyphenyl)propionate, using sulfosuccinimidyl 4-(N-maleimidomethyl)cyclohexane-1-carboxylate (sSMCC), N-[maleimidocaproyloxy]sulfosuccinimide ester (sEMCS), N-maleimidobenzoyl-N-hydroxysuccinimide ester (MBS), glutaraldehyde, 1-ethyl-3-(3-dimethylaminopropyl) carbodiimide (EDCI), Bis-diazobenzidine (BDB), or N-acetyl homocysteine thiolactone (NAHT), and others disclosed in any of U.S. Pat. Nos. 5,853,744, 5,891,506, 6,210,708, 6,617,142, 6,875, 750, 6,951,765, 7,163,677, and 7,282,194, each incorporated herein by reference. Immunoreactive proteins may be conjugated directly or indirectly to any of the commercially available support substrates having a surface coatings comprising crosslinkers, coupling agents, thiol or hydroxyl derivatizing agents, carboxyl- or amine-reactive groups such as of maleic anhydride (e.g., Pierce Immunotechnology Catalog and Handbook, at A12-A13, 1991).

In some embodiments, a protein of the invention may also be immobilized using metal chelate complexation, employing, for example, an organic chelating agent such a diethylenetriaminepentaacetic acid anhydride (DTPA); EDTA; N-chloro-p-toluenesulfonamide; and/or tetrachloro-3α-6α-diphenylglycouril-3 attached to the antibody (U.S. Pat. Nos. 4,472,509 and 4,938,948, each incorporated herein by reference). Proteins and peptides can also be immobilized by coupling to other peptides or to condensation groups immobilized on a surface or present in an immobilization buffer such as glutaraldehyde or periodate. Conjugates with fluorescence markers may also prepared in the presence of such agents or by reaction with an isothiocyanate. A peptide may be attached to a surface by conjugation, crosslinking or binding to an affinity binding agent such as biotin, streptavidin, a polysaccharide such as an alginate, a lectin, and the like.

In general, regardless of the method of preparation or immobilization status, the immunoreactive proteins disclosed herein are preferably prepared in a substantially pure form. Preferably, the immunoreactive proteins are at least about 80% pure, more preferably at least about 90% pure and most preferably at least about 99% pure.

IV. BIOLOGICAL FUNCTIONAL EQUIVALENTS

Preferred immunoreactive polypeptides or analogs thereof specifically or preferentially bind an *E. chaffeensis* or *E. canis* specific antibody. Determining whether or to what degree a particular immunoreactive polypeptide, or an analog thereof, can bind an *E. chaffeensis* or *E. canis* specific antibody can be assessed using an in vitro assay such as, for example, an enzyme-linked immunosorbent assay (ELISA), immunoblotting, immunoprecipitation, radioimmunoassay (RIA), immunostaining, latex agglutination, indirect hemagglutination assay (IHA), complement fixation, indirect immunofluorescent assay (FA), nephelometry, flow cytometry assay, chemiluminescence assay, lateral flow immunoassay, u-capture assay, mass spectrometry assay, particle-based assay, inhibition assay and/or an avidity assay.

An immunoreactive polypeptide of the present disclosure may be modified to contain amino acid substitutions, insertions and/or deletions that do not alter their respective interactions with anti-*Ehrlichia* antibody binding regions. Such a biologically functional equivalent of an immunoreactive polypeptide derived from an *Ehrlichia* protein could be a molecule having like or otherwise desirable characteristics, i.e., binding of *Ehrlichia* specific antibodies. As a nonlimiting example, certain amino acids may be substituted for other amino acids in an immunoreactive polypeptide disclosed herein without appreciable loss of interactive capacity, as demonstrated by detectably unchanged antibody binding. It is thus contemplated that an immunoreactive polypeptide disclosed herein (or a nucleic acid encoding such a polypeptide) which is modified in sequence and/or structure, but which is unchanged in biological utility or activity, remains within the scope of the present disclosure. The immunoreactive polypeptide may have, e.g., at least 90%, 95%, or 99% sequence identity with a wild-type *E. chaffeensis* polypeptide, and in some embodiments the immunoreactive protein may have 1, 2, 3, 4, 5, or more amino acid substitutions, insertions and/or deletions as compared with the corresponding wild-type *E. chaffeensis* polypeptide. In some embodiments, the mutation is a conservative substitution.

It is also well understood by the skilled artisan that, inherent in the definition of a biologically functional equivalent peptide, is the concept that there is a limit to the number of changes that may be made within a defined portion of the molecule while still maintaining an acceptable level of equivalent biological activity. Biologically functional equivalent polypeptides are thus defined herein as those peptides in which certain, not most or all, of the amino acids may be substituted. Of course, a plurality of distinct peptides with different substitutions may easily be made and used in accordance with the invention.

The skilled artisan is also aware that where certain residues are shown to be particularly important to the biological or structural properties of a peptide, e.g., residues in specific epitopes, such residues may not generally be exchanged. It is anticipated that a mutation in an immunoreactive peptide or polypeptide disclosed herein could result in a loss of species-specificity and in turn, reduce the utility of the resulting peptide for use in methods for generating an anti-*Ehrlichia* immune response. Thus, polypeptides which are antigenic (i.e., bind anti-*Ehrlichia* antibodies specifically) and comprise conservative amino acid substitutions are understood to be included in aspects of the present disclosure. Conservative substitutions are least likely to drastically alter the activity of a protein. A "conservative amino acid substitution" refers to replacement of amino acid with a chemically similar amino acid, i.e., replacing nonpolar amino acids with other nonpolar amino acids; substitution of polar amino acids with other polar amino acids, acidic residues with other acidic amino acids, etc.

Amino acid substitutions, such as those which might be employed in modifying an immunoreactive polypeptide disclosed herein are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

The invention also contemplates isoforms of the *E. chaffeensis* immunoreactive polypeptides disclosed herein. An isoform contains the same number and kinds of amino acids as an *E. chaffeensis* polypeptide as disclosed herein, but the isoform has a different molecular structure. The isoforms contemplated by the present disclosure are those having the same properties as a peptide of the invention as described herein.

Nonstandard amino acids may be incorporated into proteins by chemical modification of existing amino acids or by de novo synthesis of a polypeptide disclosed herein. A nonstandard amino acid refers to an amino acid that differs in chemical structure from the twenty standard amino acids encoded by the genetic code, and a variety of nonstandard amino acids are well known in the art.

In select embodiments, the present disclosure contemplates a chemical derivative of an immunoreactive polypeptide disclosed herein. "Chemical derivative" refers to a peptide having one or more residues chemically derivatized by reaction of a functional side group, and retaining biological activity and utility. Such derivatized polypeptides include, for example, those in which free amino groups have been derivatized to form specific salts or derivatized by alkylation and/or acylation, p-toluene sulfonyl groups, carbobenzoxy groups, t-butylocycarbonyl groups, chloroacetyl groups, formyl or acetyl groups among others. Free carboxyl groups may be derivatized to form organic or inorganic salts, methyl and ethyl esters or other types of esters or hydrazides and preferably amides (primary or secondary). Chemical derivatives may include polypeptides that comprise one or more naturally occurring amino acids derivatives of the twenty standard amino acids. For example, 4-hydroxyproline may be substituted for serine; and ornithine may be substituted for lysine.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The amino acids described herein are preferred to be in the "L" isomeric form. However, residues in the "D" isomeric form can be substituted for any L-amino acid residue, as long as the desired functional properties set forth herein are retained by the protein. In keeping with standard protein nomenclature, abbreviations for amino acid residues are known in the art.

In addition to the biological functional equivalents discussed above, it is contemplated that structurally similar compounds may be formulated to mimic the key portions of an immunoreactive peptide disclosed herein. Such compounds, which may be termed peptidomimetics, may be used in the same manner as immunoreactive peptides disclosed herein and, hence, also are functional equivalents. Methods for generating specific structures are disclosed, e.g., in Mizuno et al., 2017, as well as in U.S. Pat. Nos. 5,446,128; 5,710,245; 5,840,833; 5,859,184; 5,440,013; 5,618,914; and 5,670,155.

V. METHODS OF DETECTING *EHRLICHIA* INFECTION

Ehrlichiosis in humans generally refers to infections caused by obligate intracellular bacteria in the family Anaplasmataceae, chiefly in the genera *Ehrlichia* and *Anaplasma*. The majority of cases of human ehrlichiosis (HE) are caused by 3 distinct species: *Ehrlichia chaffeensis*, chief among them (Dumler et al., 2007). *Ehrlichia* infections in animals are also referred to as Ehrlichiosis, along with a variety of diseases caused by a diverse group of pathogens from genuses *Ehrlichia, Anaplasma, Neorickettsia*, and *Cowdria* (Dumler et al., 2007). *Ehrlichia* infections are sustained mostly in monocytes or granulocytes, and studies have demonstrated that antibodies play an essential role in the immune response to *Ehrlichia* infection (Feng and Walker, 2004; Winslow et al., 2003; Winslow et al., 2000; Yager et al., 2005).

Accordingly, select embodiments of the present disclosure provide methods of detecting antibodies that specifically bind an *Ehrlichia* organism in a sample. Such a method may involve contacting an isolated ehrlichial immunoreactive polypeptide comprising at least two peptides of Table 1 or a polypeptide of Table 2, with the test sample, under conditions that allow peptide-antibody complexes to form, and detecting the peptide-antibody complexes. In these embodiments, the detection of the peptide-antibody complexes is an indication that antibodies specific for an *Ehrlichia* organism are present in the test sample, and the absence of the peptide-antibody complexes is an indication that antibodies specific an *Ehrlichia* organism are not present in the test sample.

In multiple embodiments, the detection of an immunoreactive polypeptide disclosed herein bound to an *Ehrlichia* specific antibody (i.e., a peptide-antibody complex) may be accomplished using an enzyme-linked immunoassay (e.g., a sandwich ELISA, or a competitive ELISA), a radioimmunoassay, an immunoprecipitation, a fluorescence immunoassay, a chemiluminescent assay, an immunoblot assay, a lateral flow assay, a flow cytometry assay, a mass spectrometry assay, latex agglutination, an indirect hemagglutination assay (IHA), complement fixation, an inhibition assay, an avidity assay, a dipstick test, or a particulate-based assay. In some preferred embodiments, peptide-antibody complexes described herein are detected using an enzyme-linked immunoassay, a lateral flow assay, or a particle-based assay.

As used herein, a "sample" is any sample that comprises or is suspected to comprise antibodies. Preferably, the sample is whole blood, sputum, serum, plasma, saliva, cerebrospinal fluid or urine. In some embodiments, the sample is a blood, serum or plasma sample obtained from a subject or patient.

Ehrlichiosis caused by an *E. chaffeensis* infection in humans presents with flu-like symptoms of fever, chills, headache, and muscle aches. In more severe cases, nausea, loss of appetite, weight loss, abdominal pain, cough, diarrhea and change in mental status may also be observed. Ehrlichiosis in humans is potentially fatal.

In dogs, ehrlichiosis is most often caused by either *E. chaffeensis* or *E. canis* bacteria, and progresses in three phases: an acute phase, a subclinical phase, and a chronic phase. The acute phase normally extends weeks after infection and features symptoms similar to those of human ehrlichiosis, such as fever, lethargy, loss of appetite, shortness of breath, joint pain and stiffness, and may also include more severe symptoms such as anemia, depression, bruising, and enlarged lymph nodes, liver, and spleen. The subclinical phase can persist for years and most often presents no symptoms, although antibodies to *Ehrlichia* antigens may be detectable. The chronic phase of *Ehrlichia* infection generally features recurring symptoms of weight loss, anemia, neurological dysfunction, bleeding, ocular inflammation, leg edema, and fever, and presents a blood profile which often leads to a misdiagnosis of leukemia. An *Ehrlichia* infection that progresses to the chronic stage of disease is often fatal.

The nonspecific symptoms of an *Ehrlichia* infection and their resemblance to mild and severe influenza symptoms makes diagnosis of Ehrlichiosis difficult in humans and dogs. Diagnosis can be further hampered by current laboratory testing procedures for *Ehrlichia* infection which are not point-of-care tests, i.e., the tests are not available in most hospitals, clinics, and physician or veterinarian offices where a patient can receive treatment.

Accordingly, select embodiments of the present disclosure provide methods of identifying an *Ehrlichia* infection in a mammalian subject. Such a method may involve contacting a sample from the subject with an isolated immunoreactive polypeptide disclosed herein, e.g., comprising at least two peptides of Table 1, or more preferably a polypeptide of Table 2, under conditions that allow peptide-antibody complexes to form, and detecting the peptide-antibody complexes. In these embodiments, the detection of the peptide-antibody complexes is an indication that the subject has an *Ehrlichia* infection. The *Ehrlichia* organism may be an *E. chaffeensis* organism or an *E. canis* organism. In some embodiments, the subject is a human or a dog. As with other methods disclosed herein, the detection step may be accomplished using any appropriate type of assay known in the art, and may be preferrably accomplished using a lateral flow assay or an ELISA.

The terms "subject" and "patient" are used interchangeably herein, and may refer to a mammal, especially a human or a dog. In certain embodiments, a "subject" or "patient" refers to a mammalian *Ehrlichia* host (i.e., animal infected with an *Ehrlichia* organism). An *Ehrlichia* host may be, for example, human or non-human primate, bovine, canine, caprine, cavine, corvine, epine, equine, feline, hircine, lapine, leporine, lupine, murine, ovine, porcine, racine, vulpine, and the like, including livestock, zoological specimens, exotics, as well as companion animals, pets, and any animal under the care of a veterinary practitioner. A subject may be or may not be infected with an *Ehrlichia* organism, and a subject may be a mammal suspected of being infected with an *Ehrlichia* organism.

Without wishing to be bound by theory, the ehrlichial immunoreactive polypeptides disclosed herein each comprise at least a part of a major *Ehrlichia* epitope that accounts for a species-specific immunogenicity in humans and animals. The term "epitope" is used herein to indicate that portion of an immunogenic substance that is specifically identified, recognized, and bound by, an antibody or cell-surface receptor of a host immune system that has mounted an immune response to the immunogenic substance as determined by any method known in the art. (see, for example, Geysen et al., 1984). Thus, an epitope that is "species-specific" is an epitope that can be used to differentiate one species of the *Ehrlichia* genus from another *Ehrlichia* species.

Particular embodiments relate to determining whether a subject has been immunized against *Ehrlichia* or is actively infected with an *Ehrlichia* organism. In these embodiments, the method comprises contacting a sample from the subject with at least one isolated immunoreactive peptides of Table 1, or more preferably a polypeptide of Table 2, that is not a component of an *Ehrlichia* vaccine, and detecting whether an antibody in the sample specifically binds to the isolated ehrlichial immunoreactive polypeptide. According to the method, if an antibody in the sample specifically binds to the isolated ehrlichial immunoreactive polypeptide, then the subject has an active *Ehrlichia* infection, and if an antibody does not specifically bind to the isolated ehrlichial immunoreactive peptide, then the subject is either previously immunized with an *Ehrlichia* vaccine or is not infected with an *Ehrlichia* organism. An *Ehrlichia* organism may be an *E. chaffeensis* organism or an *E. canis* organism.

An ehrlichial immunoreactive polypeptide (e.g., comprising at least two peptides of Table 1 or a polypeptide of Table 2) may be used to bind an *Ehrlichia*-specific or *E. chaffeensis*-specific antibody using a variety of methods or kits. The specific binding between an antibody and an immunoreactive peptide of the present disclosure may therefore be assessed by any appropriate method known in the art including, but not limited to, an enzyme-linked immunosorbent assay (ELISA), a sandwich ELISA, a competitive ELISA, immunoblotting, immunoprecipitation, radioimmunoassay (RIA), immunostaining, latex agglutination, indirect hemagglutination assay (IHA), complement fixation, indirect immunofluorescent assay (FA), nephelometry, flow cytometry assay, chemiluminescence assay, lateral flow immunoassay, u-capture assay, mass spectrometry assay, particle-based assay, inhibition assay and avidity assay. Exemplary methods of detecting the binding of an *Ehrlichia*-specific antibody to an ehrlichial immunoreactive polypeptide as disclosed herein may include, for example, an ELISA performed in a microplate, a lateral flow test performed using a dipstick or lateral flow device, or a particulate-based suspension array assay performed using the Bio-Plex® system (Bio-Rad Laboratories, Hercules, Calif., USA).

A. ELISA

In certain embodiments, the detection of a peptide-antibody complex described herein is accomplished using an enzyme linked immunosorbent assay (ELISA). This assay may be performed by first contacting an ehrlichial immunoreactive polypeptide (e.g., comprising at least two peptides of Table 1 or a polypeptide of Table 2) that has been immobilized on a solid support, commonly the well of a microtiter plate, with the sample, such that antibodies specific for the peptide within the sample are allowed to bind to the immobilized peptide. Unbound sample is then removed from the immobilized peptide and a detection reagent capable of binding to the immobilized antibody-polypeptide complex is added. The amount of detection reagent that remains bound to the solid support is then determined using a method appropriate for the specific detection reagent.

In some embodiments, the detection reagent contains a binding agent (such as, for example, Protein A, Protein G, immunoglobulin, lectin or free antigen) conjugated or covalently attached to a reporter group or label. Exemplary reporter groups or labels include enzymes (such as horseradish peroxidase), substrates, cofactors, inhibitors, dyes, radionuclides, luminescent groups, fluorescent groups and biotin. The conjugation of binding agent to reporter group or label may be achieved using standard methods known to those of ordinary skill in the art. Common binding agents may also be purchased conjugated to a variety of reporter groups from many commercial sources (e.g., Zymed Laboratories, San Francisco, Calif.; and Pierce, Rockford, Ill.).

In an aspect of the present disclosure, the presence or absence of *Ehrlichia* specific antibodies may be determined in the sample by comparing the level of a signal detected from a reporter group or label in the sample with the level of a signal that corresponds to a control sample or predetermined cut-off value. In certain embodiments, the cut-off value may be the average mean signal obtained when the immobilized ehrlichial immunoreactive peptide is incubated with samples from an uninfected subject. The cut-off value may be determined using a statistical method or computer program.

B. Lateral Flow Tests

Lateral flow tests may also be referred to as immunochromatographic strip (ICS) tests or simply strip-tests. In general, a lateral flow test is a form of assay in which the test sample flows laterally along a solid substrate via capillary action, or alternatively, under fluidic control. Such tests are often inexpensive, require a very small amount (e.g., one drop) of sample, and can typically be performed reproducibly with minimal training. The economical simplicity and robustness of many lateral flow assay formats makes these types of tests ideal for identifying an *Ehrlichia* (e.g., *E. chaffeensis* or *E. canis*) infection at the point of care, which can be particularly important when the subject is, for example, a human or dog exhibiting detectable antibodies during the treatable acute phase of infection.

Exemplary lateral flow device formats include, but are not limited to, a dipstick, a card, a chip, a microslide, and a cassette, and it is widely demonstrated in the art that the choice of format is largely dependent upon the features of a particular assay. Accordingly, lateral flow devices are now ubiquitous in human and veterinarian medicine and quite varied, providing many options to the ordinarily skilled artisan for detecting a peptide-antibody complex in a sample using a lateral flow assay (See any of U.S. Pat. Nos. 7,344,893, 7,371,582, 6,136,610, and U.S. Patent Applications, 2005/0250141 and 2005/0047972, or Koczula et al. (2016) each incorporated herein by reference.) By way of a nonlimiting example, a sample from a subject suspected of having an *Ehrlichia* infection is applied to a lateral flow device comprising at least a sample zone and a binding zone. The sample may be a serum sample, and may be drawn laterally from the sample zone to the binding zone which comprises an ehrlichial immunoreactive polypeptide disclosed herein (e.g., comprising at least two peptides of Table 1 or a polypeptide of Table 2) immobilized to a surface of the lateral flow device. In this example, the binding of the immobilized ehrlichial immunoreactive polypeptide on the lateral flow device is an indication that *Ehrlichia* specific antibodies are present in the sample from the subject, indicating an *Ehrlichia* infection in the subject, such as an *E. chaffeensis* infection in the subject.

In related embodiments, an ELISA assay as described above may be performed in a rapid flow-through, lateral flow, or strip test format, wherein the antigen is immobilized on a membrane, such as a nitrocellulose membrane. In this flow-through test, *Ehrlichia* antibodies within the sample bind to the immobilized ehrlichial immunoreactive peptide as the sample passes through the membrane. A detection reagent, such as protein A labeled with gold, a fluorophore, or a chromophore, binds to the peptide-antibody complex as the solution containing the detection reagent flows through the membrane. Peptide-antibody complexes bound to detection reagent may then be detected, as appropriate for the detection reagent used (e.g., based on the presence or absence of a visibly detectable color or fluorescent label, a nanoparticle, a luminescent rare earth nanoparticle, a luminous nanoparticle, a strontium aluminate nanoparticle (e.g., see Paterson et al., 2014; and Wang et al., 2017, etc.).

In an aspect, a flow-through format ELISA may be performed in which one end of the membrane to which an ehrlichial immunoreactive peptide (e.g., comprising at least two peptides of Table 1 or a polypeptide of Table 2) is immobilized may be immersed in a solution containing the sample, or the sample may be added to an area (i.e., a sample zone) at one end of the membrane. The sample migrates along the membrane through a region (i.e., a labeling zone) comprising the detection reagent, and flows to the area (i.e., a binding zone) comprising the immobilized ehrlichial immunoreactive peptide. An accumulation of detection reagent at the binding zone indicates the presence of *Ehrlichia* specific antibodies in the sample.

Typically, a flow-through ELISA may feature a detection reagent applied to a test strip in a pattern, such as a line, that can be read visually. As with other lateral flow tests, the absence of such a pattern typically indicates a negative result. It is within the ability of an ordinarily skilled artisan to select an amount of the ehrlichial immunoreactive polypeptide for immobilization on the membrane that can generate a visually discernible pattern when the biological sample contains a level of antibodies that would be sufficient to generate a positive signal in a standard format ELISA. Preferably, the amount of peptide immobilized on the membrane ranges from about 25 ng to about 1 mg.

C. Particulate-Based Assays

In general, particle-based assays use a capture-binding partner, such as an antibody or an antigen in the case of an immunoassay, coated on the surface of particles, such as microbeads, crystals, chips, or nanoparticles. Particle-based assays may be effectively multi-plexed or modified to assay numerous variables of interest by incorporating fluorescently labeled particles or particles of different sizes in a single assay, each coated or conjugated to one or more labeled capture-binding partners. The use of sensitive detection and amplification technologies with particle-based assay platforms known in the art has resulted in numerous flexible and sensitive assay systems to choose from in performing a method described herein. For example, a multiplex particle-based assay such as the suspension array Bio-Plex® assay system available from Bio-Rad Laboratories, Inc. (Hercules, Calif.) and Luminex, Inc. (Austin, Tex.) may be useful in identifying *Ehrlichia* antibodies in a sample.

In an aspect, the present disclosure contemplates the immobilization of an isolated ehrlichial immunoreactive polypeptide (e.g., comprising at least two peptides of Table 1 or a polypeptide of Table 2) on a surface of a particle for use in a particle-based immunoassay. As described herein, methods of peptide immobilization onto support surfaces is well known in the art. In a preferred embodiment, a labeled her immunoreactive polypeptide disclosed herein is immobilized onto a surface of a particle and the peptide-particle complex is employed in an ELISA or in a flow cytometry assay according to established protocols.

VI. *EHRLICHIA* VACCINE AND IMMUNOGENIC COMPOSITIONS

Previous work has shown that Ehrlichial proteins that induce antibody responses can provide protective immune responses; thus, in some embodiments an ehrlichial protein provided herein (e.g., a polypeptide of Formula I or a polypeptide of Table 2) may be included in a pharmaceutical composition such as a vaccine composition for administration to a mammalian or human subject. For example, protection against *E. chaffeensis* infection has been demonstrated with epitope-specific antibodies directed at OMP and TRPs in in vitro models and in animal models (Kuriakose et al., 2012; Li et al., 2002; Li et al., 2001), demonstrating that ehrlichial proteins that elicit strong antibody responses to linear epitopes are protective.

In select embodiments, it is contemplated that an ehrlichial immunoreactive polypeptide of Formula I or a polypeptide of Table 2 may be comprised in a vaccine composition and administered to a subject (e.g., a human or dog) to induce a protective immune response in the subject that may substantially prevent or ameliorate infection in the subject by an *Ehrlichia* organism such as *Ehrlichia chaffeensis* or *Ehrlichia canis*. A vaccine composition for pharmaceutical use in a subject may comprise an immunoreactive polypeptide of Formula I or a polypeptide of Table 2 and a pharmaceutically acceptable carrier.

The phrases "pharmaceutical," "pharmaceutically acceptable," or "pharmacologically acceptable" refers to molecular entities and compositions that do not produce an adverse, allergic or other untoward reaction when administered to an animal, such as, for example, a human, as appropriate. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1289-1329, 1990, incorporated herein by reference). Except insofar as any conventional carrier is incompatible with the active ingredient, its use in the vaccine compositions of the present disclosure is contemplated.

As used herein, a "protective immune response" refers to a response by the immune system of a mammalian host to an *Ehrlichia* antigen which results in increased recognition of the antigen and antibody production by the immune system of the mammalian host upon subsequent exposure to an *Ehrlichia* pathogen. A protective immune response may substantially reduce or prevent symptoms as a result of a subsequent exposure to *Ehrlichia chaffeensis* or *Ehrlichia canis*.

In some embodiments, a vaccine composition of the present disclosure may comprise an immunoreactive polypeptide (e.g., having a sequence that has at least about 90%, 91%, 92%, 93%, 94%, 95%, 96%, 97%, 98%, 99%, or 100% sequence identity to a polypeptide of Formula I or a polypeptide of Table 2). In some embodiments, a vaccine composition comprising the immunoreactive polypeptide may be used to induce a protective immune response against *Ehrlichia chaffeensis* (e.g., in a human or dog subject).

A person having ordinary skill in the medical arts will appreciate that the actual dosage amount of a vaccine composition administered to an animal or human patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, vaccine compositions may comprise, for example, at least about 0.1% of an ehrlichial immunoreactive polypeptide comprising or consisting of a polypeptide of Formula I or Table 2. In other embodiments, the active compound may comprise between about 2% to about 75% of the weight of the unit, or between about 25% to about 60%, for example, and any range derivable therein. As with many vaccine compositions, frequency of administration, as well as dosage, will vary among members of a population of animals or humans in ways that are predictable by one skilled in the art of immunology. By way of non-limiting example, the pharmaceutical compositions and vaccines may be administered by injection (e.g., intracutaneous, intramuscular, intravenous or subcutaneous), intranasally (e.g., by aspiration) or orally. Between 1 and 3 doses may be administered over a 1-36 week period. In some embodiments, 3 doses are administered, at intervals of 3-4 months, and booster vaccinations may be given periodically thereafter.

In some embodiments, a "suitable dose" is an amount of an immunoreactive polypeptide that, when administered as described above, is capable of raising an immune response in an immunized patient sufficient to protect the subject from an *Ehrlichia* infection in subsequent exposures to *Ehrlichia* organisms. In general, the amount of peptide present in a suitable dose (or produced in situ by the nucleic acid in a dose) may range from about 1 μg to about 500 mg per kg of host, typically from about 10 μg to about 10 mg, preferably from about 100 μg to about 1 mg and more preferably from about 100 μg to about 100 microgram.

A vaccine composition of the present disclosure may comprise different types of carriers depending on whether it is to be administered in solid, liquid or aerosol form, and whether it needs to be sterile for such routes of administration as injection. A vaccine composition disclosed herein can be administered intramuscularly, intradermally, subcutaneously, intravenously, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subconjunctivally, intravesicularly, mucosally, intrapericardially, locally, orally, intranasally, or by inhalation, injection, infusion, continuous infusion, lavage, or localized perfusion. A vaccine composition may also be administered to a subject via a catheter, in cremes, in lipid compositions, by ballistic particulate delivery, or by other method or any combination of the forgoing as would be known to one of ordinary skill in the art (see, for example, Remington: The Science and Practice of Pharmacy, 21$^{st}$ Ed. Lippincott Williams and Wilkins, 2005, incorporated herein by reference).

While any suitable carrier known to those of ordinary skill in the art may be employed in the vaccine compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Of particular interest, in some embodiments, is a vaccine composition that may be administered by microstructured transdermal or ballistic particulate delivery. Microstructures as carriers for vaccine formulation are a desirable configuration for vaccine applications and are widely known in the art (e.g., U.S. Pat. Nos. 5,797,898, 5,770,219 and 5,783,208, and U.S. Patent Application 2005/0065463). Such a vaccine composition formulated for ballistic particulate delivery may comprise an isolated immunoreactive polypeptide of Table 1, 2, or 3 immobilized on a surface of a support substrate. In these embodiments, a support substrate can include, but is not limited to, a microcapsule, a microparticle, a microsphere, a nanocapsule, a nanoparticle, a nanosphere, or a combination thereof.

Microstructures or ballistic particles that serve as a support substrate for an ehrlichial immunoreactive polypeptide disclosed herein may be comprised of biodegradable material and non-biodegradable material, and such support substrates may be comprised of synthetic polymers, silica, lipids, carbohydrates, proteins, lectins, ionic agents, cross-linkers, and other microstructure components available in the art. Protocols and reagents for the immobilization of a peptide of the invention to a support substrate composed of such materials are widely available commercially and in the art.

In other embodiments, a vaccine composition comprises an immobilized or encapsulated immunoreactive polypeptide of Formula I or a polypeptide of Table 2 and a support substrate. In these embodiments, a support substrate can include, but is not limited to, a lipid microsphere, a lipid nanoparticle, an ethosome, a liposome, a niosome, a phospholipid, a sphingosome, a surfactant, a transferosome, an emulsion, or a combination thereof. The formation and use of liposomes and other lipid nano- and microcarrier formulations is generally known to those of ordinary skill in the art, and the use of liposomes, microparticles, nanocapsules and the like have gained widespread use in delivery of therapeutics (e.g., U.S. Pat. No. 5,741,516, specifically incorporated herein in its entirety by reference). Numerous methods of liposome and liposome-like preparations as potential drug carriers, including encapsulation of peptides, have been reviewed (U.S. Pat. Nos. 5,567,434; 5,552,157; 5,565,213; 5,738,868 and 5,795,587, each of which is specifically incorporated in its entirety by reference).

In addition to the methods of delivery described herein, a number of alternative techniques are also contemplated for administering the disclosed vaccine compositions. By way of nonlimiting example, a vaccine composition may be administered by sonophoresis (i.e., ultrasound) which has been used and described in U.S. Pat. No. 5,656,016 for enhancing the rate and efficacy of drug permeation into and through the circulatory system; intraosseous injection (U.S. Pat. No. 5,779,708), or feedback-controlled delivery (U.S. Pat. No. 5,697,899), and each of the patents in this paragraph is specifically incorporated herein in its entirety by reference.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, Bortadella pertussis or *Mycobacterium tuberculosis*. Suitable adjuvants are commercially available as, for example, Freund's Incomplete Adjuvant and Freund's Complete Adjuvant (Difco Laboratories, Detroit, Mich.) and Merck Adjuvant 65 (Merck and Company, Inc., Rahway, N.J.). Other suitable adjuvants include alum, biodegradable microspheres, monophosphoryl lipid A and quil A.

A polypeptide may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids such as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

Sterile injectable solutions are prepared by incorporating the active peptides in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less than 0.5 ng/mg protein.

In particular embodiments, prolonged absorption of an injectable composition can be brought about by the use in the compositions of agents delaying absorption, such as, for example, aluminum monostearate, gelatin or combinations thereof.

A. *Ehrlichia* Bacterin

In some embodiments, an immunogenic or vaccine composition as disclosed herein comprises an *Ehrlichia* bacterin, such as an *E. Canis* bacterin or an *E. chaffeensis* bacterin. E Canis bacterin may be prepared by heat-inactivating or chemically-inactivating the *Ehrlichia* bacteria.

A variety of methods may be used to generate an *E. chaffeensis* or *E. Canis* bacterin. For example, the bacteria may be inactivated by heat or psoralen in the presence of ultraviolet light to produce the bacterin. The effective immunizing amount of the inactivated *Ehrlichia* bacterin can vary depending upon the chosen strain or strains. It is anticipated that any amount of an *Ehrlichia* bacterin, alone or in combination with (i) chimeric polypeptide as disclosed herein (e.g., a polypeptide of Formula I or of Table 2), and/or (ii) adjuvant(s), sufficient to evoke a protective immune response may be used in various embodiments (e.g., to induce a protective immune response in a subject). In some embodiments, a dosage unit comprising at least about $1 \times 10^4$ TCID$_{50}$ inactivated *E. chaffeensis* and/or *E. Canis* bacterin can be used. Additional methods that may be used to generate an *Ehrlichia* bacterin include, but are not limited to, treatment of an *E. chaffeensis* or *E. Canis* with heat, formaldehyde, formalin, bi-ethylene amine, radiation, and/or beta-propiolactone treatment. It is anticipated that the bacterin may be inactivated by any suitable method available. Additional methods that may be used to generate an *Ehrlichia* or *E. Canis* bacterin include those described, e.g., in WO2005087803, EP2433646, Vega et al., 2007; or Stuen et al., 2015.

In some embodiments, the *Ehrlichia* bacterin comprises inactivated crude antigen based on inactivated *E. chaffeensis* and/or *E. Canis* bacteria. For example, in some embodiments, frozen buffy coat (e.g., 10 ml frozen buffy coat) containing *E. chaffeensis* or E. *Canis* may be obtained, and the material was inactivated using 0.3% formaldehyde for 48 h at room temperature. Thereafter, the material can tested for lack of infectivity by in vitro methods or by using an in vivo animal model. Methods for inactivating bacteria using formaldehyde are further described in Tollersrud et al., 2001.

The resulting *Ehrlichia* bacterin can be included with (i) 1, 2, 3, or more chimeric immunogenic proteins or peptides as described herein (e.g., as described in Table 2) and/or (ii) an adjuvant, to form an immunogenic or vaccine composition. For example, the inactivated *E. Canis* bacterin may be prepared as a suspension and then included in an emulsion adjuvant, e.g., as described below.

B. Adjuvants

In some aspects, an immunogenic composition comprising one or more chimeric polypeptide as disclosed herein (e.g., a polypeptide of Formula I or of Table 2) also contains an adjuvant. In some embodiments, the composition is a pharmaceutical preparation or a vaccine composition. A variety of adjuvants are known that can be included. For example, adjuvants such as MF59, AS01, AS02, AS03, AS04, Virosomes, CAF01, CAF04, CAF05, Montanide ISA™ 720, or Montanide ISA™ 51 (e.g., Bonam et al., 2017) can be used in some embodiments.

In some embodiments, the immunogenic or vaccine composition includes an adjuvant comprising a triterpenoid, sterol, immunomodulator, polymer, and/or Th2 stimulator. For example, in some embodiments the adjuvant comprises DEAE Dextran, an immunostimulatory oligonucleotide, and oil (e.g., a light mineral oil), wherein the immunostimulatory oligonucleotide is a CpG containing ODN, and wherein the adjuvant formulation is a water-in-oil (W/O) emulsion. The vaccine adjuvant may optionally comprise an *Ehrlichia* bacterin (such as a heat-inactivated E. *Canis* or *E. chaffeensis*) and/or a chimeric peptide as disclosed herein (e.g., of Formula I or Table 2). In some embodiments, the immunogenic or vaccine composition includes an antigen component and an adjuvant formulation comprising a saponin (e.g., present in an amount of about 1 µg to about 5,000 µg per dose), a sterol (e.g., present in an amount of about 1 µg to about 5,000 µg per dose), a quaternary ammonium compound (e.g., present in an amount of about 1 µg to about 5,000 .mu.g per dose), a polymer (e.g., present in an amount of about 0.0001% v/v to about 75% v/v.), and an ORN/ODN; the saponin may be Quil A or a purified faction thereof, the sterol may be cholesterol, the quaternary ammonium compound may be dimethyl dioctadecyl ammonium bromide (DDA), the polymer may be polyacrylic acid, and the ORN/ODN may be a CpG. The adjuvant may comprise a glycolipid, such N-(2-deoxy-2-L-leucylamino-β-D-glucopyranosyl)-N-octadecyldodecanamide acetate. The adjuvant may comprise an immunostimulatory oligonucleotide, a polyacrylic acid polymer and at least two of the following: (a) dimethyl dioctadecyl ammonium bromide (DDA); (b) a sterol; and/or (c) N-(2-deoxy-2-L-leucylamino-β-D-glucopyranosyl)-N-octadecyldodecanamide acetate. For example, the vaccine composition may comprise an adjuvant as described, e.g., in U.S. Pat. Nos. 10,238,736, 8,580,280, or US Publication 2019/0008953.

In some embodiments, immunogenic or vaccine composition includes an antigen component and an adjuvant formulation comprising a triterpenoid saponin, a sterol, a quaternary ammonium compound, and a polyacrylic acid polymer, wherein the antigen component comprises or consists of a *Ehrlichia* bacterin (such as a heat-inactivated *E. Canis*) and/or a chimeric polypeptide as disclosed herein (e.g., a polypeptide of Formula I or of Table 2). In some embodiments, the saponin is present in an amount of about 1 mg to about 5,000 mg per dose, the sterol is present in an amount of about 1 mg to about 5,000 mg per dose, the quaternary ammonium compound is present in an amount of about 1 mg to about 5,000 mg per dose, and the polyacrylic acid polymer is present in an amount of about 0.0001% v/v to about 75% v/v. For example, the vaccine composition may comprise an adjuvant as described, e.g., in U.S. Pat. No. 9,662,385.

In some aspects, an immunogenic or vaccine composition as disclosed herein comprises an oil-based adjuvant comprising an *Ehrlichia* bacterin (such as a heat-inactivated E. *Canis* or *E. chaffensis*) and/or one or more chimeric polypeptide as disclosed herein (e.g., a polypeptide of Formula I or of Table 2). For example, the adjuvant formulation may comprise an oily phase and an aqueous phase, a polycationic carrier (e.g., DEAE dextran), and a CpG containing immunostimulatory oligonucleotide, wherein the vaccine is a water-in-oil emulsion. The adjuvant may optionally further comprise an aluminum hydroxide gel. In some embodiments, the CpG containing immunostimulatory oligonucleotide is present in the amount of about 50 to about 400 µg per dose and DEAE Dextran is present in the amount of about 10 to about 300 mg per dose. The adjuvant formulation may comprise an immunostimulating oligonucleotide, polycationic carrier, sterol, saponin, quaternary amine, TLR-3 agonist, glycolipid, and/or MPL-A (or an analog thereof) in an oil emulsion. For example, the vaccine composition may comprise an adjuvant as described, e.g., in U.S. Pat. No. 10,117,921 or US 2019/0038737.

In some embodiments, the immunogenic composition is an emulsion comprising (i) an *Ehrlichia* bacterin (such as a heat-inactivated *E. Canis* or *E. chaffeensis*), and/or (ii) one or more chimeric polypeptide as disclosed herein (e.g., a polypeptide of Formula I or of Table 2). For example, the emulsion composition may comprise an adjuvant, such as acrylic polymer and/or dimethyl dioctadecyl ammonium bromide (DDA), in the aqueous phase. The emulsion can be prepared, in some embodiments, by mixing an aqueous phase containing the antigen (e.g., an *E. Canis* bacterin such as a heat-inactivated *E. Canis*, and/or one or more chimeric polypeptide (e.g., a polypeptide of Formula I or of Table 2)) and adjuvant with an oil phase in the presence of an emulsifier. In some embodiments, the adjuvant component comprises an oil-in-water emulsion, wherein the aqueous phase of the oil-in-water emulsion comprises dimethyl dioctadecyl ammonium bromide (DDA) and/or an alkyl-polyacrylic acid (alkyl-PAA). In some embodiments, the oil in the oil-in-water emulsion is mineral oil, a terpene oil, soybean oil, olive oil, or a propylene glycol derivative. The adjuvant may further comprise the adjuvant component further comprises CpG DNA, a lipopolysaccharide, and/or monophosphoryl lipid A. The vaccine may further comprise one or more emulsifiers. For example, the vaccine composition may comprise an adjuvant as described, e.g., in U.S. Pat. No. 9,545,439 or 8,980,288.

The adjuvant may be a liposome or emulsion formulation. The liposomes may be unilamellar, multilamellar, or multivesicular. In some embodiments, the an immunogenic or vaccine composition comprises a lipid or lipid-containing adjuvant. In some embodiments, the liposomes are cationic liposomes. In various embodiments, adjuvants such as MF59 (e.g., Calabro et al. (2013) *Vaccine* 31: 3363-3369), AS01 (Didierlaurent, et al. (2014) *J. Immunol.* 193, 1920-1930), AS02 (Garçon and Van Mechelen (2011) *Expert Rev. Vaccines* 10, 471-486), AS03 (Morel, S. et al. (2011) *Vaccine* 29, 2461-2473), AS04 (Didierlaurent, et al. (2009) *J. Immunol.* 183: 6186-6197.), Virosomes (Künzi, et al. (2009) *Vaccine* 27, 3561-3567), CAF01 (Tandrup Schmidt, et al. (2016) *Pharmaceutics* 8, 7.), CAF04 (Billeskov, et al. (2016) *PLoS One* 11, e0161217), CAF05 (Billeskov, et al. (2016) *PLoS One* 11, e0161217), Montanide ISA™ 720 (Aucouturier, et al. (2002) *Expert Rev. Vaccines* 1, 111-118), or Montanide ISA™ 51 (Aucouturier, et al. (2002) *Expert Rev. Vaccines* 1, 111-118) can be used. Table 3 provides a listing of example adjuvant containing formulations that can be used in various embodiments.

TABLE 3

Example adjuvant containing formulations

| Adjuvant | Composition |
| --- | --- |
| MF59 | Squalene, Span 85, Tween 80, and citrate buffer |
| AS01 | Liposomes containing 3-O-desacyl-4'-monophosphoryl lipid A (MPLA) and QS21 |
| AS02 | Oil-in-water (O/W) emulsion containing MPLA and the saponin QS21 |
| AS03 | α-tocopherol, squalene, polysorbate 80, and PBS |
| AS04 | Contains MPLA adsorbed onto a particulate form of aluminum salt |
| Virosomes | Contain inactivated virus |
| CAF01 | Cationic liposomal vehicle containing dimethyl dioctadecyl-ammonium (DDA) with a glycolipid immunostimulator (TDB) |
| CAF04 | Cationic liposomal vehicle containing DDA with monomycoloyl glycerol analog (MMG) |
| CAF05 | Cationic liposomal vehicle containing DDA with the immunostimulators TDB and poly(I:C) |
| Montanide ISA ™ 720 | Water-in-oil (W/O) emulsion containing non-mineral oil with mannide mono-oleate family emulsifier |
| Montanide ISA ™ 51 | W/O emulsion containing mineral oil with mannide mono-oleate family emulsifier |
| Acrylic polymer/ DDA emulsions | Oil-in-water emulsion comprises dimethyl dioctadecyl ammonium bromide (DDA) and/or an alkyl-polyacrylic acid (alkyl-PAA); e.g., see U.S. Pat. No. 9,545,439 or U.S. Pat. No. 8,980,288. |
| CpG/DEAE emulsions | Emulsions comprising a polycationic carrier (e.g., DEAE dextran) and a CpG containing immunostimulatory oligonucleotide; e.g., see U.S. Pat. No. 10,117,921 or US 2019/0038737. |
| Saponin/cholesterol/ DDA adjuvants | Saponin (e.g., Quil A), cholesterol, DDA, a polyacrylic acid; e.g., a triterpenoid saponin, a sterol, a quaternary ammonium compound, and a polyacrylic acid polymer; e.g., see U.S. Pat. No. 9,662,385. |
| Polyacrylic acid polymer emulsions | Water-in-oil (W/O) emulsions, DEAE Dextran, immunostimulatory oligonucleotide (e.g., a CpG containing ODN), a sterol, N-(2-deoxy-2-L-leucylamino-β-D-glucopyranosyl)-N-octadecyldodecanamide acetate, and/or a polyacrylic acid polymer; e.g., see U.S. Pat. No. 10,238,736, U.S. Pat. No. 8,580,280, or US Publication 2019/0008953. |

VII. *EHRLICHIA* DETECTION AND VACCINATION KITS

Various embodiments of the present disclosure are concerned with kits for the detection of antibodies in a sample that specifically bind an *Ehrlichia* organism, such as *E. chaffeensis* or *E. canis*. The kits may thus be used for the diagnosis or identification of an *Ehrlichia* infection in a subject. In other embodiments, the invention provides kits for determining whether a subject has been immunized against *Ehrlichia* or is actively infected with an *Ehrlichia* organism. In still other embodiments, kits are provided for vaccination of a subject against *E. chaffeensis* infection, and in some embodiments it is anticipated that the composition may be used to provide a protective immune response against an *E. canis* infection.

In select embodiments, a kit of the present disclosure may be used to perform a method disclosed herein. For example, a kit may be suitable for detecting *Ehrlichia* antibodies in a sample, for identifying an *Ehrlichia* infection individual, for determining whether a subject has been immunized against *Ehrlichia* or is actively infected with an *Ehrlichia* organism, or for vaccinating a subject against an *Ehrlichia* organism. In these embodiments, one or more immunoreactive peptide (e.g., comprising a polypeptide of Formula I or a polypeptide of Table 2, or a polypeptide having at least about 95% or more sequence identity with a polypeptide of Formula I or a polypeptide of Table 2) may be comprised in the kit. The ehrlichial immunoreactive polypeptide in the kit may be detectably labeled or immobilized on a surface of a support substrate also comprised in the kit. The immunoreactive polypeptide(s) may, for example, be provided in the kit in a suitable form, such as sterile, lyophilized, or both.

The support substrate comprised in a kit of the invention may be selected based on the method to be performed. By way of nonlimiting example, a support substrate may be a multi-well plate or microplate, a membrane, a filter, a paper, an emulsion, a bead, a microbead, a microsphere, a nanobead, a nanosphere, a nanoparticle, an ethosome, a liposome, a niosome, a transferosome, a dipstick, a card, a celluloid strip, a glass slide, a microslide, a biosensor, a lateral flow apparatus, a microchip, a comb, a silica particle, a magnetic particle, or a self-assembling monolayer.

As appropriate to the method being performed, a kit may further comprise one or more apparatuses for delivery of a composition to a subject or for otherwise handling a composition of the invention. By way of nonlimiting example, a kit may include an apparatus that is a syringe, an eye dropper, a ballistic particle applicator (e.g., applicators disclosed in U.S. Pat. Nos. 5,797,898, 5,770,219 and 5,783,208, and U.S. Patent Application 2005/0065463), a scoopula, a microslide cover, a test strip holder or cover, and such like.

A detection reagent for labeling a component of the kit may optionally be comprised in a kit for performing a method of the present disclosure. In particular embodiments, the labeling or detection reagent is selected from a group comprising reagents used commonly in the art and including, without limitation, radioactive elements, enzymes, molecules which absorb light in the UV range, and fluorophores such as fluorescein, rhodamine, auramine, Texas Red, AMCA blue and *Lucifer* Yellow. In other embodiments, a kit is provided comprising one or more container means and a BST protein agent already labeled with a detection reagent selected from a group comprising a radioactive element, an enzyme, a molecule which absorbs light in the UV range, and a fluorophore.

In particular embodiments, the present disclosure provides a kit for detecting anti-*Ehrlichia* antibodies in a sample which may also be used for identification of an *Ehrlichia* infection in a subject, and/or for determining whether a subject has been immunized against *Ehrlichia* or is actively infected with an *Ehrlichia* organism. Such a kit may comprise one or more immunoreactive polypeptides (e.g., comprising a polypeptide of Formula I or a polypeptide of Table 2, or having at least about 95% or more sequence identity with a polypeptide comprising a polypeptide of Formula I or a polypeptide of Table 2), and the peptides may be detectably labeled and immobilized to one or more support substrates comprised in the kit.

In some embodiments, a kit comprises an immunoreactive polypeptide comprising a polypeptide of Formula I or a polypeptide of Table 2 or having about 95% or more sequence identity with polypeptide comprising a polypeptide of Formula I or a polypeptide of Table 2. The peptides may be immobilized to one or more separate lateral flow assay devices, such as a nitrocellulose test strips. In these embodiments, each of the test strips may further comprises a detection reagent, for example, a chromophore-labeled protein A. Such a kit may further comprise one or more containers for sample material, one or more diluents for sample dilution, and one or more control indicator strips for comparison.

When reagents and/or components comprising a kit are provided in a lyophilized form (lyophilisate) or as a dry powder, the lyophilisate or powder can be reconstituted by the addition of a suitable solvent. In particular embodiments, the solvent may be a sterile, pharmaceutically acceptable buffer and/or other diluent. It is envisioned that such a solvent may also be provided as part of a kit.

When the components of a kit are provided in one and/or more liquid solutions, the liquid solution may be, by way of non-limiting example, a sterile, aqueous solution. The compositions may also be formulated into an administrative composition. In this case, the container means may itself be a syringe, pipette, topical applicator or the like, from which the formulation may be applied to an affected area of the body, injected into a subject, and/or applied to or mixed with the other components of the kit.

IV. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Methods

Chimera Construction and Cloning

Sequences representing five *Ehrlichia* epitope chimeras were synthesized commercially (GenScript). The chimeric sequences were cloned into pET-14 and the recombinant chimeric protein expressed in *E. coli* BL21 (DE) or BL21-AI (Invitrogen) (Table 1).

Imidazole) and sonicated on ice for 5 min, then lysates were cleared by centrifugation for 1 h at 12,000×g at 4° C. His-tagged proteins were purified by incubating for 30 min with his-resin, and washed 3 times with wash buffer (10 mM Imidazole in lysis buffer), and protein was eluted with elution buffer (250 mM Imidazole in lysis buffer).

Western Blot

Protein samples for Western immunoblot analysis were resolved by SDS-PAGE, transferred to nitrocellulose membrane, blocked in Tris-buffered saline (TBS) containing 5% non-fat dry milk. Proteins were reacted with dog anti-*E. canis* or anti-*E. chaffeensis* serum (1:500). Blots were incubated with phosphatase-labeled goat anti-dog IgG diluted in TBS (1:5000) (Kirkegaard & Perry, Gaithersburg, Mass.) and proteins reactivity visualized after addition of alkaline phosphatase substrate (Kirkegaard & Perry).

ELISA

Sera from human patients infected with *E. chaffeensis* and dogs infected with *E. canis* were used to evaluate *Ehrlichia* chimera immunoreactivity. An ELISA was performed by incubating 50 ng/well of chimeric protein diluted in PBS in 96-well ELISA plates (PolySorp, Nunc) and incubated overnight at 4 C. The plates were washed 3× with 0.2% Tween 20 in TBS (TBST) and blocked 100 ul of blocking buffer (10% horse serum in TBST) and incubated at room temperature for 1 h with shaking. Plates were washed 3× with TBST, and 50 ul of primary antibody diluted 1:100 in blocking buffer was incubated at room temperature for 1 h with shaking. Plates were washed 3× with TBST, add 50 ul of secondary antibody AP-conjugate diluted in blocking buffer and incubate at room temperature for 1 h with shaking. Substrate was added and incubated at room temperature for 30 min with shaking in the dark and OD was determined using an ELISA plate reader @650 nm.

Results

Five *Ehrlichia* chimeric constructs were expressed in *E. coli* and the recombinant protein purified (FIGS. 1-5). Purified *E. canis* or *E. chaffeensis* specific chimeric proteins reacted with antibodies in dog anti-*E. canis* or anti-*E. chaffeensis* (FIGS. 1-3). Similarly, *E. canis/E. chaffeensis* combination chimeric proteins reacted strongly with both anti-*E. canis* and anti-*E. chaffeensis* dog sera demonstrating functionality of species specific epitopes represented in the chimera (FIG. 4 and FIG. 5). ELISA was performed with a panel of convalescent anti-*E. chaffeensis* patient sera to demonstrate immunoreactivity of chimeric proteins with

TABLE 1

*Ehrlichia* chimeras

| Chimera Name | MW | pI | Vector | Expression cell | Tag | Solubility |
| --- | --- | --- | --- | --- | --- | --- |
| *E. chaff* TRP32/TRP120/A34 | 30.8 KD | 3.79 | pET-14b | BL21-(DE3) | His | Soluble |
| *E. canis* TRP140/TRP36/TRP19 | 22.8 KD | 3.94 | pET-14b | BL21-(DE3) | His | Soluble |
| *E. canis* TRP36/TRP140 | 17.8 KD | 3.93 | pET-14b | BL21-AI | His | Soluble |
| *Ehrlichia* TRP32/TRP120/TRP36/TRP140/P28/HSP | 31.4 KD | 4.13 | pET-14b | BL21-(DE3) | His | Soluble |
| *Ehrlichia* TRP120/TRP140/TRP36/P28 | 27.9 KD | 4.09 | pET-14b | BL21-AI | His | Soluble |

Chimera Expression and Purification

*Ehrlichia* chimera recombinant proteins were purified under native conditions using Roche cOmplete™ His-Tag Protein Purification Protocol. Briefly, *E. coli* cell pellets were resuspended in lysis buffer (50 mM Tris-HCl, 150 mM NaCl, 2 mMDTT, 2 mM MgCl2, 5 mM EDTA and 5 mM antibodies. The *E. chaffeensis* TRP32/TRP120/A34 chimera reacted strongly with 10 HME patient sera demonstrating high immunoreactivity with all HME patient sera (FIG. 1). Two *E. canis* specific chimeras (TRP140/TRP36/TRP19 and TRP36/TRP140) were reacted with 10 sera from dogs naturally infected with *E. canis*. All sera from *E. canis*- infected dogs reacted strongly with the chimeric constructs (FIG. 2 and FIG. 3). The *E. chaffeensis/E. canis* combination chimeras immunoreactivity were tested with dog-anti-*E. canis* sera and human anti-*E. chaffeensis* patient sera. Both chimeras reacted strongly with anti-*E. canis* and anti-*E. chaffeensis* antibodies demonstrating the functionality of the species-specific epitopes represented within the chimera with *E. canis* and *E. chaffeensis* antibodies (FIG. 4 and FIG. 5).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 9,545,439
U.S. Pat. No. 9,545,439
U.S. Pat. No. 10,117,921
U.S. Pat. No. 10,117,921
U.S. Pat. No. 10,117,921
U.S. Pat. No. 10,238,736
U.S. Pat. No. 4,220,450
U.S. Pat. No. 4,373,932
U.S. Pat. No. 4,472,509
U.S. Pat. No. 4,897,268
U.S. Pat. No. 4,938,948
U.S. Pat. No. 5,075,109
U.S. Pat. No. 5,440,013
U.S. Pat. No. 5,446,128
U.S. Pat. No. 5,470,723
U.S. Pat. No. 5,470,932
U.S. Pat. No. 5,543,504
U.S. Pat. No. 5,552,157
U.S. Pat. No. 5,565,213
U.S. Pat. No. 5,567,434
U.S. Pat. No. 5,618,914
U.S. Pat. No. 5,656,016
U.S. Pat. No. 5,670,155
U.S. Pat. No. 5,697,899
U.S. Pat. No. 5,738,868
U.S. Pat. No. 5,741,516
U.S. Pat. No. 5,770,219
U.S. Pat. No. 5,779,708
U.S. Pat. No. 5,783,208
U.S. Pat. No. 5,795,587
U.S. Pat. No. 5,797,898
U.S. Pat. No. 5,840,833
U.S. Pat. No. 5,853,744
U.S. Pat. No. 5,859,184
U.S. Pat. No. 5,891,506
U.S. Pat. No. 5,929,237
U.S. Pat. No. 6,136,610
U.S. Pat. No. 6,210,708
U.S. Pat. No. 6,372,445
U.S. Pat. No. 6,617,142
U.S. Pat. No. 6,875,750
U.S. Pat. No. 6,951,765
U.S. Pat. No. 7,163,677
U.S. Pat. No. 7,282,194
U.S. Pat. No. 7,344,893
U.S. Pat. No. 7,371,582
U.S. Pat. No. 8,580,280
U.S. Pat. No. 8,980,288
U.S. Pat. No. 8,980,288
U.S. Pat. No. 9,662,385.
U.S. Patent Appln. 2005/0047972
U.S. Patent Appln. 2005/0065463
U.S. Patent Appln. 2005/0250141
U.S. Patent Appln. 2007/0264664
U.S. Patent Appln. 2009/0005535
U.S. Patent Appln. 2019/0008953
U.S. Patent Appln. 2019/0038737
EP2433646
WO2005087803

Aucouturier, et al., *Expert Rev. Vaccines*, 1, 111-118, 2002.
Billeskov, et al., *PLoS One* 11, e0161217, 2016.
Bonam et al., *Trends in Pharmacological Sciences*, 38(9): 771-778, 2017.
Calabro et al., *Vaccine*, 31: 3363-3369, 2013.
Carpino et al., *Org. Proc. Res. Dev.*, 7(1)28-37, 2003.
Didierlaurent, et al., *J. Immunol.*, 183: 6186-6197, 2009.
Didierlaurent, et al., *J. Immunol.*, 193, 1920-1930, 2013
Dumler et al., *Clin. Infect. Dis.*, 45:S45-S51, 2007.
Feng and Walker, *Infect. Immun.*, 72:966-971, 2004.
Fishbein et al., Human ehrlichiosis in the United States, 1985 to 1990. AnnInternMed 120:736-743, 1994.
Garçon and Van Mechelen, *Expert Rev. Vaccines*, 10, 471-486, 2011.
Geysen et al., *Proc. Natl. Acad. Sci. USA*, 81(13):3998-4002, 1984.
He et al., Vaxign: the first web-based vaccine design program for reverse vaccinology and applications for vaccine development. J Biomed Biotechnol 2010:297505, 2010.
Koczula et al., 2016.
Künzi, et al., *Vaccine*, 27, 3561-3567, 2009.
Kuriakose et al., *Ehrlichia chaffeensis* transcriptome in mammalian and arthropod hosts reveals differential gene expression and post transcriptional regulation. PLoS One 6:e24136, 2011.
Kuriakose et al., Molecular basis of antibody mediated immunity against *Ehrlichia chaffeensis* involves species-specific linear epitopes in tandem repeat proteins. Microbes Infect 14:1054-1063, 2012.
Li and Winslow, Survival, replication, and antibody susceptibility of *Ehrlichia chaffeensis* outside of host cells. InfectImmun 71:4229-4237, 2003.
Li et al., Antibodies highly effective in SCID mice during infection by the intracellular bacterium *Ehrlichia chaffeensis* are of picomolar affinity and exhibit preferential epitope and isotype utilization. J Immunol 169:1419-1425, 2002.
Li et al., Outer membrane protein-specific monoclonal antibodies protect SCID mice from fatal infection by the obligate intracellular bacterial pathogen *Ehrlichia chaffeensis*. J Immunol 166:1855-1862, 2001.

Lin et al., Global proteomic analysis of two tick-borne emerging zoonotic agents: *Anaplasma phagocytophilum* and *Ehrlichia chaffeensis*. Front Microbiol 2:24, 2011.

Magnan et al., High-throughput prediction of protein antigenicity using protein microarray data. Bioinformatics 26:2936-2943, 2010.

McBride and Walker, Progress and obstacles in vaccine development for the ehrlichioses. Expert Rev Vaccines 9:1071-1082, 2010.

Mizuno et al., Chemistry. 23(58):14394-14409, Oct. 17, 2017.

Morel, S. et al., *Vaccine*, 29, 2461-2473, 2011.

Nandi et al., CD4 T-cell epitopes associated with protective immunity induced following vaccination of mice with an ehrlichial variable outer membrane protein. InfectImmun 75:5453-5459., 2007.

Olano et al., Human monocytotropic ehrlichiosis, Missouri. EmergInfectDis 9:1579-1586, 2003.

Paparone et al., Ehrlichiosis with pancytopenia and ARDS. New Jersey Med 92:381-385, 1995.

Paterson et al., Anal Chem. 86(19):9481-8, Oct. 7, 2014.

Pierce Immunotechnology Catalog and Handbook, at A12-A13, 1991

Racine et al., IgM production by bone marrow plasmablasts contributes to long-term protection against intracellular bacterial infection. J Immunol 186:1011-1021, 2011.

Remington's Pharmaceutical Sciences, 18th Ed. Mack Printing Company, 1289-1329, 1990.

Sotomay et al., Animal model of fatal human monocytotropic ehrlichiosis. AmJPath 158:757-769, 2001.

Stuen et al., *Acta Vet Scand.*, 57:40, 2015.

Tandrup Schmidt, et al., *Pharmaceutics*, 8, 7, 2016.

The Science and Practice of Pharmacy, 21$^{st}$ Ed. Lippincott Williams and Wilkins, 2005.

Tollersrud et al., *Vaccine*, 19:3896-3903, 2001.

Vega et al., *Vaccine*, 25:519-525, 2007.

Walker and Dumler, Human monocytic and granulocytic ehrlichioses. Discovery and diagnosis of emerging tick-borne infections and the critical role of the pathologist. [Review] [50 refs]. Archives of Pathology & Laboratory Medicine 121:785-791, 1997.

Walker et al., *Ehrlichia chaffeensis*: a prevalent, life-threatening, emerging pathogen. Trans Am Clin Climatol Assoc 115:375-382; discussion 382-374, 2004.

Wang et al., 2017.

Winslow et al., *Ann. NY Acad. Sci.*, 990:435-443, 2003.

Winslow et al., *Infect. Immun.*, 68:2187-2195, 2000.

Winslow et al., Infection of the laboratory mouse with the intracellular pathogen *Ehrlichia chaffeensis*. InfectImmun 66:3892-3899, 1998.

Yager et al., *Infect. Immun.*, 73:8009-8016, 2005.

Zemella et al., *Cell-Free Protein Synthesis: Pros and Cons of Prokaryotic and Eukaryotic Systems. Chembiochem.;* 16(17):2420-2431, 2015.

---

What is claimed is:

1. An isolated polypeptide, wherein the isolated polypeptide comprises:
   (i) immunogenic sequences TRP120 (SEQ ID NO:22) and TRP75 (SEQ ID NO:19), or sequences at least 90% identical; and
   (ii) wherein at least one of the immunogenic sequences is contiguously repeated in the polypeptide.

2. The isolated polypeptide of claim 1, wherein each of the TRP120 (SEQ ID NO: 22) and TRP75 (SEQ ID NO: 19), or a sequence at least 90% identical are contiguously repeated 1, 2, 3, 4, 5, 6, or 7 times in the polypeptide.

3. The isolated polypeptide of claim 1, wherein the isolated polypeptide comprises one or more of (SEQ ID NOs:11-16 or 36-42), wherein the one or more of (SEQ ID NOs:11-16 or 36-42) are contiguously repeated 0, 1, 2, or 3 times.

4. The isolated polypeptide of claim 1, wherein each of the immunogenic sequences are contiguously repeated from 1 to 3 times in the polypeptide.

5. The isolated polypeptide of claim 4, wherein each of the immunogenic sequences are contiguously repeated from 1 to 2 times in the polypeptide.

6. The isolated peptide of claim 1, wherein the isolated polypeptide comprises TRP140 (SEQ ID NO:23), A34N1 (SEQ ID NO:7), TRP63 (SEQ ID NO:18), TRP47 (SEQ ID NO:17), TRP28 (SEQ ID NO:2), TRP36R1 (SEQ ID NO:8), TRP36R2 (SEQ ID NO:9), TRP36R3 (SEQ ID NO:10), TRP36CO (SEQ ID NO:36), TRP19 (SEQ ID NO:1), HSP (SEQ ID NO:24), or a sequence at least 90% identical; wherein each of the immunogenic sequences are contiguously repeated from 1 to 7 times in the polypeptide.

7. The polypeptide of claim 1, wherein the isolated polypeptide comprises TRP36, TRP140, TRP28, or HSP.

8. The polypeptide of claim 7, wherein the TRP36R1 if present is repeated 2-6 times, and wherein the other immunogenic sequences are repeated 1-3 times.

9. The polypeptide of claim 8, wherein the polypeptide comprises all of TRP32, TRP120, TRP36, TRP140, TRP28, and HSP.

10. The polypeptide of claim 9, wherein the polypeptide comprises SEQ ID NO:28.

11. The polypeptide of claim 1, wherein the isolated polypeptide comprises at least three, at least four, at least five or all of TRP32R1, TRP32R2, TRP32R3, TRP32R4, TRP120, and A34N1.

12. The polypeptide of claim 11, wherein TRP120 and A34N1 are each contiguously repeated 1-3 times.

13. The polypeptide of claim 12, wherein TRP120 and A34N1 are each contiguously repeated 2 times.

14. The polypeptide of claim 1, wherein the polypeptide comprises A34N1, TRP47, and/or TRP63.

15. The polypeptide of claim 14, wherein the polypeptide comprises A34N1.

16. The polypeptide of claim 1, wherein the polypeptide comprises TRP36R1, TRP140, TRP95R, and/or TRP95C.

17. The polypeptide of claim 1, wherein the polypeptide comprises a polypeptide of SEQ ID NOs: 25-35.

18. The polypeptide of claim 1, wherein the isolated polypeptide comprises A34N1, TRP63, TRP47, TRP75, TRP28, TRP36, TRP19, TRP140, and/or HSP.

19. The polypeptide of claim 1, wherein the polypeptide further comprises at least two of TRP36R1, TRP36R2, TRP36R3, and/or TRP36CO.

20. The polypeptide of claim 1, wherein the different immunogenic sequences are not separated by a linker or a spacer.

21. The polypeptide of claim 1, wherein the different immunogenic sequences are separated by a linker or a spacer.

22. The polypeptide of claim 21, wherein the linker is a glycine linker.

23. The polypeptide of claim 22, wherein the glycine linker has the amino acid sequence -(G)$_X$-, wherein X=3-5.

24. The polypeptide of claim 1, wherein the polypeptide is comprised in a pharmaceutical preparation.

25. The pharmaceutical preparation of claim 24, wherein the pharmaceutical preparation is formulated for parenteral, intravenous, subcutaneous, intranasal, sublingual, or intradermal administration.

26. The polypeptide of claim 1, wherein the polypeptide is attached to a solid support or comprised in a diagnostic kit.

27. The polypeptide of claim 26, wherein the solid support is glass or plastic.

28. The polypeptide of claim 26, wherein the solid support is comprised in a lateral flow assay, or microfluidic device.

29. An isolated polypeptide of Formula I ($A_s$-$B_t$—$C_u$-$D_v$-$E_w$-$F_x$-$G_y$-$H_z$)$_n$,
   wherein A, B, C, D, E, F, G, and H is a peptide selected from SEQ ID NOs:1-24 and 36-42, or a sequence at least 90% identical to any one of (SEQ ID NOs:1-24 or 36-42),
   wherein s, t, u, v, x, y, and z is an integer 0-8, wherein at least two of s-z are ≥1 and at least one of s-z is ≥2, and wherein n is an integer 1-5;
   wherein the polypeptide comprises TRP120 (SEQ ID NO:22) and TRP75 (SEQ ID NO:19).

30. A pharmaceutical preparation comprising the polypeptide of claim 1 and a pharmaceutically acceptable excipient.

31. A method of detecting antibodies that specifically bind an *Ehrlichia* organism in a test sample, comprising: (a) contacting an isolated polypeptide of claim 1; (b) detecting the peptide-antibody complexes; wherein the detection of the peptide-antibody complexes is an indication that antibodies specific for an *Ehrlichia* organism are present in the test sample, and wherein the absence of the peptide-antibody complexes is an indication that antibodies specific an *Ehrlichia* organism are not present in the test sample.

32. A method of identifying an *Ehrlichia* infection in a mammalian subject comprising: (a) contacting a biological sample from the subject with an isolated polypeptide of claim 1 under conditions that allow peptide-antibody complexes to form; and (b) detecting the peptide-antibody complexes; wherein the detection of the peptide-antibody complexes is an indication that the subject has an *Ehrlichia* infection.

33. A method of inducing an immune response in a mammalian subject comprising administering to the subject an effective amount of a pharmaceutical preparation comprising a polypeptide of a pharmaceutical composition of claim 30.

34. A method of treating an *Ehrlichia chaffeensis* or *Ehrlichia canis* infection in a subject comprising:
   (a) contacting a biological sample from the subject with an isolated polypeptide of claim 1 under conditions that allow peptide-antibody complexes to form;
   (b) detecting the peptide-antibody complexes; wherein the detection of the peptide-antibody complexes is an indication that the subject has an *Ehrlichia chaffeensis* or *Ehrlichia canis* infection; and
   (c) administering a therapeutic compound to treat *Ehrlichia* infection in the subject.

35. The polypeptide of claim 1, wherein the polypeptide comprises A34N1, TRP63, and TRP75.

36. The polypeptide of claim 35, wherein the polypeptide comprises SEQ ID NO:34.

* * * * *

```
SEQUENCE LISTING

<160> NUMBER OF SEQ ID NOS: 47

<210> SEQ ID NO 1
<211> LENGTH: 24
<212> TYPE: PRT
<213> ORGANISM: Ehrlichia canis

<400> SEQUENCE: 1

His Phe Thr Gly Pro Thr Ser Phe Glu Val Asn Leu Ser Glu Glu Glu
1               5                   10                  15

Lys Met Glu Leu Gln Glu Val Ser
            20

<210> SEQ ID NO 2
<211> LENGTH: 21
<212> TYPE: PRT
<213> ORGANISM: Ehrlichia canis

<400> SEQUENCE: 2

Ala Lys Glu Glu Lys Asn Ala Thr Ala Lys Thr Phe Gln Leu Lys Gly
1               5                   10                  15

Asp Trp Asp Gly Ala
            20

<210> SEQ ID NO 3
<211> LENGTH: 30
<212> TYPE: PRT
<213> ORGANISM: Ehrlichia chaffeensis

<400> SEQUENCE: 3

Ser Asp Leu His Glu Ser Ser Phe Val Glu Leu Pro Gly Pro Ser Lys
1               5                   10                  15

Glu Glu Val Gln Phe Glu Asp Asp Ala Lys Asn Val Val Tyr
            20                  25                  30
```

<210> SEQ ID NO 4
<211> LENGTH: 30
<212> TYPE: PRT
<213> ORGANISM: Ehrlichia chaffeensis

<400> SEQUENCE: 4

Ser Asp Leu His Gly Ser Phe Ser Val Glu Leu Phe Asp Pro Ser Lys
1               5                   10                  15

Glu Glu Val Gln Leu Glu Ser Asp Leu Gln Gln Ser Ser Asn
            20                  25                  30

<210> SEQ ID NO 5
<211> LENGTH: 30
<212> TYPE: PRT
<213> ORGANISM: Ehrlichia chaffeensis

<400> SEQUENCE: 5

Ser Asp Leu His Gly Ser Phe Ser Val Glu Leu Phe Asp Pro Phe Lys
1               5                   10                  15

Glu Ala Val Gln Leu Gly Asn Asp Leu Gln Gln Ser Ser Asp
            20                  25                  30

<210> SEQ ID NO 6
<211> LENGTH: 30
<212> TYPE: PRT
<213> ORGANISM: Ehrlichia chaffeensis

<400> SEQUENCE: 6

Ser Asp Ser His Glu Pro Ser His Leu Glu Leu Pro Ser Leu Ser Glu
1               5                   10                  15

Glu Val Ile Gln Leu Glu Ser Asp Leu Gln Gln Ser Ser Asn
            20                  25                  30

<210> SEQ ID NO 7
<211> LENGTH: 26
<212> TYPE: PRT
<213> ORGANISM: Ehrlichia chaffeensis

<400> SEQUENCE: 7

Val Arg Ser Ile Thr Asp Pro Arg Ile Val Gln Gln Glu Ala Asp
1               5                   10                  15

Gln Gln Gln Glu Val Gln Gln Gln Ala Asp
            20                  25

<210> SEQ ID NO 8
<211> LENGTH: 9
<212> TYPE: PRT
<213> ORGANISM: Ehrlichia canis

<400> SEQUENCE: 8

Thr Glu Asp Ser Val Ser Ala Pro Ala
1               5

<210> SEQ ID NO 9
<211> LENGTH: 8
<212> TYPE: PRT
<213> ORGANISM: Ehrlichia canis

<400> SEQUENCE: 9

Ala Ser Val Val Pro Glu Ala Glu
1               5

-continued

```
<210> SEQ ID NO 10
<211> LENGTH: 9
<212> TYPE: PRT
<213> ORGANISM: Ehrlichia canis

<400> SEQUENCE: 10

Thr Glu Asp Pro Val Ser Ala Thr Ala
1               5

<210> SEQ ID NO 11
<211> LENGTH: 26
<212> TYPE: PRT
<213> ORGANISM: Artificial sequence
<220> FEATURE:
<223> OTHER INFORMATION: Synthetic peptide

<400> SEQUENCE: 11

Thr Glu Asp Ser Val Ser Ala Pro Ala Ala Ser Val Val Pro Glu Ala
1               5                   10                  15

Glu Thr Glu Asp Pro Val Ser Ala Thr Ala
            20                  25

<210> SEQ ID NO 12
<211> LENGTH: 26
<212> TYPE: PRT
<213> ORGANISM: Artificial sequence
<220> FEATURE:
<223> OTHER INFORMATION: Synthetic peptide

<400> SEQUENCE: 12

Thr Glu Asp Ser Val Ser Ala Pro Ala Thr Glu Asp Pro Val Ser Ala
1               5                   10                  15

Thr Ala Ala Ser Val Val Pro Glu Ala Glu
            20                  25

<210> SEQ ID NO 13
<211> LENGTH: 26
<212> TYPE: PRT
<213> ORGANISM: Artificial sequence
<220> FEATURE:
<223> OTHER INFORMATION: Synthetic peptide

<400> SEQUENCE: 13

Ala Ser Val Val Pro Glu Ala Glu Thr Glu Asp Ser Val Ser Ala Pro
1               5                   10                  15

Ala Thr Glu Asp Pro Val Ser Ala Thr Ala
            20                  25

<210> SEQ ID NO 14
<211> LENGTH: 26
<212> TYPE: PRT
<213> ORGANISM: Artificial sequence
<220> FEATURE:
<223> OTHER INFORMATION: Synthetic peptide

<400> SEQUENCE: 14

Ala Ser Val Val Pro Glu Ala Glu Thr Glu Asp Pro Val Ser Ala Thr
1               5                   10                  15

Ala Thr Glu Asp Ser Val Ser Ala Pro Ala
            20                  25

<210> SEQ ID NO 15
<211> LENGTH: 26
<212> TYPE: PRT
<213> ORGANISM: Artificial sequence
```

-continued

```
<220> FEATURE:
<223> OTHER INFORMATION: Synthetic peptide

<400> SEQUENCE: 15

Thr Glu Asp Pro Val Ser Ala Thr Ala Thr Glu Asp Ser Val Ser Ala
1               5                   10                  15

Pro Ala Ala Ser Val Val Pro Glu Ala Glu
            20                  25

<210> SEQ ID NO 16
<211> LENGTH: 26
<212> TYPE: PRT
<213> ORGANISM: Artificial sequence
<220> FEATURE:
<223> OTHER INFORMATION: Synthetic peptide

<400> SEQUENCE: 16

Thr Glu Asp Pro Val Ser Ala Thr Ala Ala Ser Val Val Pro Glu Ala
1               5                   10                  15

Glu Thr Glu Asp Ser Val Ser Ala Pro Ala
            20                  25

<210> SEQ ID NO 17
<211> LENGTH: 19
<212> TYPE: PRT
<213> ORGANISM: Ehrlichia chaffeensis

<400> SEQUENCE: 17

Ala Ser Val Ser Glu Gly Asp Ala Val Val Asn Ala Val Ser Gln Glu
1               5                   10                  15

Thr Pro Ala

<210> SEQ ID NO 18
<211> LENGTH: 20
<212> TYPE: PRT
<213> ORGANISM: Ehrlichia chaffeensis

<400> SEQUENCE: 18

Ser Leu Phe Thr Glu Glu Glu Lys Ile Leu Ala Ile Leu Ser Ala Arg
1               5                   10                  15

Phe Ile Cys Lys
            20

<210> SEQ ID NO 19
<211> LENGTH: 18
<212> TYPE: PRT
<213> ORGANISM: Ehrlichia chaffeensis

<400> SEQUENCE: 19

Asp Val Lys Asp Asn Lys Pro Ser Asp Val Lys Leu Pro Val Ile Lys
1               5                   10                  15

Ala Glu

<210> SEQ ID NO 20
<211> LENGTH: 24
<212> TYPE: PRT
<213> ORGANISM: Ehrlichia canis

<400> SEQUENCE: 20

Asp Asp Ser Lys Leu Pro Val Ile Lys Val Glu Asp Lys Ser Lys Leu
1               5                   10                  15

Gln Asp Thr Lys Asp Lys Lys Arg
```

-continued

```
<210> SEQ ID NO 21
<211> LENGTH: 19
<212> TYPE: PRT
<213> ORGANISM: Ehrlichia canis

<400> SEQUENCE: 21

Lys Lys Ile Lys Glu Tyr Asp Glu Asp Tyr Thr Ile Thr Tyr Tyr
1               5                   10                  15

Asp Asp Asp

<210> SEQ ID NO 22
<211> LENGTH: 22
<212> TYPE: PRT
<213> ORGANISM: Ehrlichia chaffeensis

<400> SEQUENCE: 22

Ser Lys Val Glu Gln Glu Glu Thr Asn Pro Glu Val Leu Ile Lys Asp
1               5                   10                  15

Leu Gln Asp Val Ala Ser
            20

<210> SEQ ID NO 23
<211> LENGTH: 25
<212> TYPE: PRT
<213> ORGANISM: Ehrlichia canis

<400> SEQUENCE: 23

Glu His Ser Ser Ser Glu Val Gly Glu Lys Val Ser Glu Thr Ser Lys
1               5                   10                  15

Glu Glu Asn Thr Pro Glu Val Lys Ala
            20                  25

<210> SEQ ID NO 24
<211> LENGTH: 21
<212> TYPE: PRT
<213> ORGANISM: Ehrlichia chaffeensis

<400> SEQUENCE: 24

Tyr Gly Ala Pro Glu Ile Thr Lys Asp Gly Tyr Lys Val Ile Lys Ser
1               5                   10                  15

Ile Lys Pro Glu Asp
            20

<210> SEQ ID NO 25
<211> LENGTH: 264
<212> TYPE: PRT
<213> ORGANISM: Ehrlichia chaffeensis

<400> SEQUENCE: 25

Ser Asp Leu His Glu Ser Ser Phe Val Glu Leu Pro Gly Pro Ser Lys
1               5                   10                  15

Glu Glu Val Gln Phe Glu Asp Asp Ala Lys Asn Val Val Tyr Ser Asp
                20                  25                  30

Leu His Gly Ser Phe Ser Val Glu Leu Phe Asp Pro Ser Lys Glu Glu
            35                  40                  45

Val Gln Leu Glu Ser Asp Leu Gln Gln Ser Ser Asn Ser Asp Leu His
        50                  55                  60

Gly Ser Phe Ser Val Glu Leu Phe Asp Pro Phe Lys Glu Ala Val Gln
65                  70                  75                  80
```

-continued

```
Leu Gly Asn Asp Leu Gln Gln Ser Ser Asp Ser Asp Ser His Glu Pro
                85                  90                  95
Ser His Leu Glu Leu Pro Ser Leu Ser Glu Val Ile Gln Leu Glu
            100                 105                 110
Ser Asp Leu Gln Gln Ser Ser Asn Ser Lys Val Glu Gln Glu Thr
        115                 120                 125
Asn Pro Glu Val Leu Ile Lys Asp Leu Gln Asp Val Ala Ser Lys Val
130                 135                 140
Gln Glu Glu Thr Asn Pro Glu Val Leu Ile Lys Asp Leu Gln Asp
145                 150                 155                 160
Val Ala Ser Lys Val Glu Gln Glu Glu Thr Asn Pro Glu Val Leu Ile
                165                 170                 175
Lys Asp Leu Gln Asp Val Ala Ser Val Arg Ser Ile Thr Asp Pro Arg
            180                 185                 190
Ile Val Val Gln Gln Glu Ala Asp Gln Gln Glu Val Gln Gln Gln
        195                 200                 205
Ala Asp Ser Val Arg Ser Ile Thr Asp Pro Arg Ile Val Val Gln Gln
210                 215                 220
Glu Ala Asp Gln Gln Gln Glu Val Gln Gln Ala Asp Ser Val Arg
225                 230                 235                 240
Ser Ile Thr Asp Pro Arg Ile Val Val Gln Gln Glu Ala Asp Gln Gln
                245                 250                 255
Gln Glu Val Gln Gln Gln Ala Asp
            260

<210> SEQ ID NO 26
<211> LENGTH: 201
<212> TYPE: PRT
<213> ORGANISM: Ehrlichia canis

<400> SEQUENCE: 26

His Phe Thr Gly Pro Thr Ser Phe Glu Val Asn Leu Ser Glu Glu
1               5                   10                  15
Lys Met Glu Leu Gln Glu Val Ser Thr Glu Asp Ser Val Ser Ala Pro
            20                  25                  30
Ala Thr Glu Asp Ser Val Ser Ala Pro Ala Glu His Ser Ser Glu
        35                  40                  45
Val Gly Glu Lys Val Ser Glu Thr Ser Lys Glu Glu Asn Thr Pro Glu
    50                  55                  60
Val Lys Ala His Phe Thr Gly Pro Thr Ser Phe Glu Val Asn Leu Ser
65                  70                  75                  80
Glu Glu Lys Met Glu Leu Gln Glu Val Ser Thr Glu Asp Ser Val
                85                  90                  95
Ser Ala Pro Ala Thr Glu Asp Ser Val Ser Ala Pro Ala Glu His Ser
            100                 105                 110
Ser Ser Glu Val Gly Glu Lys Val Ser Glu Thr Ser Lys Glu Glu Asn
        115                 120                 125
Thr Pro Glu Val Lys Ala His Phe Thr Gly Pro Thr Ser Phe Glu Val
    130                 135                 140
Asn Leu Ser Glu Glu Lys Met Glu Leu Gln Glu Val Ser Thr Glu
145                 150                 155                 160
Asp Ser Val Ser Ala Pro Ala Thr Glu Asp Ser Val Ser Ala Pro Ala
                165                 170                 175
Glu His Ser Ser Ser Glu Val Gly Glu Lys Val Ser Glu Thr Ser Lys
```

-continued

```
                180                 185                 190
Glu Glu Asn Thr Pro Glu Val Lys Ala
            195                 200

<210> SEQ ID NO 27
<211> LENGTH: 172
<212> TYPE: PRT
<213> ORGANISM: Ehrlichia canis

<400> SEQUENCE: 27

Thr Glu Asp Ser Val Ser Ala Pro Ala Thr Glu Asp Ser Val Ser Ala
1               5                   10                  15

Pro Ala Thr Glu Asp Ser Val Ser Ala Pro Ala Thr Glu Asp Ser Val
            20                  25                  30

Ser Ala Pro Ala Thr Glu Asp Ser Val Ser Ala Pro Ala Thr Glu Asp
        35                  40                  45

Ser Val Ser Ala Pro Ala Thr Glu Asp Ser Val Ser Ala Pro Ala Thr
    50                  55                  60

Glu Asp Ser Val Ser Ala Pro Ala Glu His Ser Ser Glu Val Gly
65                  70                  75                  80

Glu Lys Val Ser Glu Thr Ser Lys Glu Glu Asn Thr Pro Glu Val Lys
                85                  90                  95

Ala Glu His Ser Ser Glu Val Gly Glu Lys Val Ser Glu Thr Ser
            100                 105                 110

Lys Glu Glu Asn Thr Pro Glu Val Lys Ala Glu His Ser Ser Glu
        115                 120                 125

Val Gly Glu Lys Val Ser Glu Thr Ser Lys Glu Glu Asn Thr Pro Glu
    130                 135                 140

Val Lys Ala Glu His Ser Ser Glu Val Gly Glu Lys Val Ser Glu
145                 150                 155                 160

Thr Ser Lys Glu Glu Asn Thr Pro Glu Val Lys Ala
                165                 170

<210> SEQ ID NO 28
<211> LENGTH: 274
<212> TYPE: PRT
<213> ORGANISM: Artificial sequence
<220> FEATURE:
<223> OTHER INFORMATION: Synthetic peptide

<400> SEQUENCE: 28

Ser Asp Leu His Gly Ser Phe Ser Val Glu Leu Phe Asp Pro Phe Lys
1               5                   10                  15

Glu Ala Val Gln Leu Gly Asn Asp Leu Gln Gln Ser Ser Asp Ser Asp
            20                  25                  30

Leu His Gly Ser Phe Ser Val Glu Leu Phe Asp Pro Phe Lys Glu Ala
        35                  40                  45

Val Gln Leu Gly Asn Asp Leu Gln Gln Ser Ser Asp Ser Lys Val Glu
    50                  55                  60

Gln Glu Glu Thr Asn Pro Glu Val Leu Ile Lys Asp Leu Gln Asp Val
65                  70                  75                  80

Ala Ser Ser Lys Val Glu Gln Glu Glu Thr Asn Pro Glu Val Leu Ile
                85                  90                  95

Lys Asp Leu Gln Asp Val Ala Ser Thr Glu Asp Ser Val Ser Ala Pro
            100                 105                 110

Ala Thr Glu Asp Ser Val Ser Ala Pro Ala Thr Glu Asp Ser Val Ser
        115                 120                 125
```

```
Ala Pro Ala Thr Glu Asp Ser Val Ser Ala Pro Ala Glu His Ser Ser
        130                 135                 140

Ser Glu Val Gly Glu Lys Val Ser Glu Thr Ser Lys Glu Glu Asn Thr
145                 150                 155                 160

Pro Glu Val Lys Ala Glu His Ser Ser Ser Glu Val Gly Glu Lys Val
                165                 170                 175

Ser Glu Thr Ser Lys Glu Glu Asn Thr Pro Glu Val Lys Ala Ala Lys
                180                 185                 190

Glu Glu Lys Asn Ala Thr Ala Lys Thr Phe Gln Leu Lys Gly Asp Trp
            195                 200                 205

Asp Gly Ala Ala Lys Glu Glu Lys Asn Ala Thr Ala Lys Thr Phe Gln
        210                 215                 220

Leu Lys Gly Asp Trp Asp Gly Ala Tyr Gly Ala Pro Glu Ile Thr Lys
225                 230                 235                 240

Asp Gly Tyr Lys Val Ile Lys Ser Ile Lys Pro Glu Asp Tyr Gly Ala
                245                 250                 255

Pro Glu Ile Thr Lys Asp Gly Tyr Lys Val Ile Lys Ser Ile Lys Pro
                260                 265                 270

Glu Asp
```

<210> SEQ ID NO 29
<211> LENGTH: 258
<212> TYPE: PRT
<213> ORGANISM: Artificial sequence
<220> FEATURE:
<223> OTHER INFORMATION: Synthetic peptide

<400> SEQUENCE: 29

```
Ser Lys Val Glu Gln Glu Glu Thr Asn Pro Glu Val Leu Ile Lys Asp
1                   5                   10                  15

Leu Gln Asp Val Ala Ser Ser Lys Val Glu Gln Glu Glu Thr Asn Pro
            20                  25                  30

Glu Val Leu Ile Lys Asp Leu Gln Asp Val Ala Ser Ser Lys Val Glu
        35                  40                  45

Gln Glu Glu Thr Asn Pro Glu Val Leu Ile Lys Asp Leu Gln Asp Val
    50                  55                  60

Ala Ser Glu His Ser Ser Ser Glu Val Gly Glu Lys Val Ser Glu Thr
65                  70                  75                  80

Ser Lys Glu Glu Asn Thr Pro Glu Val Lys Ala Glu His Ser Ser Ser
                85                  90                  95

Glu Val Gly Glu Lys Val Ser Glu Thr Ser Lys Glu Glu Asn Thr Pro
            100                 105                 110

Glu Val Lys Ala Glu His Ser Ser Ser Glu Val Gly Glu Lys Val Ser
        115                 120                 125

Glu Thr Ser Lys Glu Glu Asn Thr Pro Glu Val Lys Ala Thr Glu Asp
    130                 135                 140

Ser Val Ser Ala Pro Ala Thr Glu Asp Ser Val Ser Ala Pro Ala Thr
145                 150                 155                 160

Glu Asp Ser Val Ser Ala Pro Ala Thr Glu Asp Ser Val Ser Ala Pro
                165                 170                 175

Ala Thr Glu Asp Ser Val Ser Ala Pro Ala Thr Glu Asp Ser Val Ser
                180                 185                 190

Ala Pro Ala Ala Lys Glu Glu Lys Asn Ala Thr Ala Lys Thr Phe Gln
            195                 200                 205
```

```
Leu Lys Gly Asp Trp Asp Gly Ala Ala Lys Glu Glu Lys Asn Ala Thr
    210                 215                 220

Ala Lys Thr Phe Gln Leu Lys Gly Asp Trp Asp Gly Ala Ala Lys Glu
225                 230                 235                 240

Glu Lys Asn Ala Thr Ala Lys Thr Phe Gln Leu Lys Gly Asp Trp Asp
            245                 250                 255

Gly Ala

<210> SEQ ID NO 30
<211> LENGTH: 183
<212> TYPE: PRT
<213> ORGANISM: Ehrlichia chaffeensis

<400> SEQUENCE: 30

Ser Lys Val Glu Gln Glu Glu Thr Asn Pro Glu Val Leu Ile Lys Asp
1               5                   10                  15

Leu Gln Asp Val Ala Ser Ser Lys Val Glu Gln Glu Glu Thr Asn Pro
            20                  25                  30

Glu Val Leu Ile Lys Asp Leu Gln Asp Val Ala Ser Gly Gly Gly Val
        35                  40                  45

Arg Ser Ile Thr Asp Pro Arg Ile Val Gln Glu Ala Asp Gln
    50                  55                  60

Gln Gln Glu Val Gln Gln Ala Asp Val Arg Ser Ile Thr Asp Pro
65                  70                  75                  80

Arg Ile Val Val Gln Gln Glu Ala Asp Gln Gln Gln Glu Val Gln Gln
                85                  90                  95

Gln Ala Asp Gly Gly Ser Leu Phe Thr Glu Glu Lys Ile Leu
            100                 105                 110

Ala Ile Leu Ser Ala Arg Phe Ile Cys Lys Ser Leu Phe Thr Glu Glu
        115                 120                 125

Glu Lys Ile Leu Ala Ile Leu Ser Ala Arg Phe Ile Cys Lys Gly Gly
    130                 135                 140

Gly Ala Ser Val Ser Glu Gly Asp Ala Val Val Asn Ala Val Ser Gln
145                 150                 155                 160

Glu Thr Pro Ala Ala Ser Val Ser Glu Gly Asp Ala Val Val Asn Ala
                165                 170                 175

Val Ser Gln Glu Thr Pro Ala
            180

<210> SEQ ID NO 31
<211> LENGTH: 142
<212> TYPE: PRT
<213> ORGANISM: Ehrlichia chaffeensis

<400> SEQUENCE: 31

Ser Lys Val Glu Gln Glu Glu Thr Asn Pro Glu Val Leu Ile Lys Asp
1               5                   10                  15

Leu Gln Asp Val Ala Ser Ser Lys Val Glu Gln Glu Glu Thr Asn Pro
            20                  25                  30

Glu Val Leu Ile Lys Asp Leu Gln Asp Val Ala Ser Gly Gly Gly Val
        35                  40                  45

Arg Ser Ile Thr Asp Pro Arg Ile Val Val Gln Gln Glu Ala Asp Gln
    50                  55                  60

Gln Gln Glu Val Gln Gln Ala Asp Val Arg Ser Ile Thr Asp Pro
65                  70                  75                  80

Arg Ile Val Val Gln Gln Glu Ala Asp Gln Gln Gln Glu Val Gln Gln
```

```
                    85                  90                  95
Gln Ala Asp Gly Gly Ser Leu Phe Thr Glu Glu Lys Ile Leu
            100                 105                 110

Ala Ile Leu Ser Ala Arg Phe Ile Cys Lys Ser Leu Phe Thr Glu Glu
            115                 120                 125

Glu Lys Ile Leu Ala Ile Leu Ser Ala Arg Phe Ile Cys Lys
            130                 135                 140

<210> SEQ ID NO 32
<211> LENGTH: 140
<212> TYPE: PRT
<213> ORGANISM: Ehrlichia chaffeensis

<400> SEQUENCE: 32

Ser Lys Val Glu Gln Glu Glu Thr Asn Pro Glu Val Leu Ile Lys Asp
1               5                   10                  15

Leu Gln Asp Val Ala Ser Ser Lys Val Glu Gln Glu Glu Thr Asn Pro
            20                  25                  30

Glu Val Leu Ile Lys Asp Leu Gln Asp Val Ala Ser Gly Gly Gly Val
        35                  40                  45

Arg Ser Ile Thr Asp Pro Arg Ile Val Gln Gln Glu Ala Asp Gln
    50                  55                  60

Gln Gln Glu Val Gln Gln Ala Asp Val Arg Ser Ile Thr Asp Pro
65                  70                  75                  80

Arg Ile Val Val Gln Gln Glu Ala Asp Gln Gln Gln Glu Val Gln Gln
                85                  90                  95

Gln Ala Asp Gly Gly Gly Ala Ser Ser Glu Gly Asp Ala Val Val
            100                 105                 110

Asn Ala Val Ser Gln Glu Thr Pro Ala Ala Ser Val Ser Glu Gly Asp
            115                 120                 125

Ala Val Val Asn Ala Val Ser Gln Glu Thr Pro Ala
            130                 135                 140

<210> SEQ ID NO 33
<211> LENGTH: 136
<212> TYPE: PRT
<213> ORGANISM: Ehrlichia chaffeensis

<400> SEQUENCE: 33

Val Arg Ser Ile Thr Asp Pro Arg Ile Val Val Gln Gln Glu Ala Asp
1               5                   10                  15

Gln Gln Gln Glu Val Gln Gln Ala Asp Val Arg Ser Ile Thr Asp
            20                  25                  30

Pro Arg Ile Val Val Gln Gln Glu Ala Asp Gln Gln Gln Glu Val Gln
        35                  40                  45

Gln Gln Ala Asp Gly Gly Gly Ser Leu Phe Thr Glu Glu Lys Ile
    50                  55                  60

Leu Ala Ile Leu Ser Ala Arg Phe Ile Cys Lys Ser Leu Phe Thr Glu
65                  70                  75                  80

Glu Glu Lys Ile Leu Ala Ile Leu Ser Ala Arg Phe Ile Cys Lys Gly
                85                  90                  95

Gly Gly Ala Ser Val Ser Glu Gly Asp Ala Val Val Asn Ala Val Ser
            100                 105                 110

Gln Glu Thr Pro Ala Ala Ser Val Ser Glu Gly Asp Ala Val Val Asn
            115                 120                 125

Ala Val Ser Gln Glu Thr Pro Ala
```

-continued

```
            130                 135

<210> SEQ ID NO 34
<211> LENGTH: 134
<212> TYPE: PRT
<213> ORGANISM: Ehrlichia chaffeensis

<400> SEQUENCE: 34

Val Arg Ser Ile Thr Asp Pro Arg Ile Val Gln Gln Glu Ala Asp
1               5                   10                  15

Gln Gln Gln Glu Val Gln Gln Ala Asp Val Arg Ser Ile Thr Asp
                20                  25                  30

Pro Arg Ile Val Gln Gln Ala Asp Gln Gln Glu Val Gln
            35                  40                  45

Gln Gln Ala Asp Gly Gly Gly Ser Leu Phe Thr Glu Glu Lys Ile
    50                  55                  60

Leu Ala Ile Leu Ser Ala Arg Phe Ile Cys Lys Ser Leu Phe Thr Glu
65                  70                  75                  80

Glu Glu Lys Ile Leu Ala Ile Leu Ser Ala Arg Phe Ile Cys Lys Gly
                85                  90                  95

Gly Gly Asp Val Lys Asp Asn Lys Pro Ser Asp Val Lys Leu Pro Val
            100                 105                 110

Ile Lys Ala Glu Asp Val Lys Asp Asn Lys Pro Ser Asp Val Lys Leu
            115                 120                 125

Pro Val Ile Lys Ala Glu
            130

<210> SEQ ID NO 35
<211> LENGTH: 163
<212> TYPE: PRT
<213> ORGANISM: Ehrlichia canis

<400> SEQUENCE: 35

Thr Glu Asp Ser Val

```
<211> LENGTH: 28
<212> TYPE: PRT
<213> ORGANISM: Ehrlichia canis

<400> SEQUENCE: 36
```

Glu Ala Ser Val Val Pro Ala Ala Glu Ala Pro Gln Pro Ala Gln Gln
1               5                   10                  15

Thr Glu Asp Glu Phe Phe Ser Asp Gly Ile Glu Ala
            20                  25

```
<210> SEQ ID NO 37
<211> LENGTH: 37
<212> TYPE: PRT
<213> ORGANISM: Artificial sequence
<220> FEATURE:
<223> OTHER INFORMATION: Synthetic peptide

<400> SEQUENCE: 37
```

Glu Ala Ser Val Val Pro Ala Ala Glu Ala Pro Gln Pro Ala Gln Gln
1               5                   10                  15

Thr Glu Asp Glu Phe Phe Ser Asp Gly Ile Glu Ala Thr Glu Asp Ser
            20                  25                  30

Val Ser Ala Pro Ala
        35

```
<210> SEQ ID NO 38
<211> LENGTH: 37
<212> TYPE: PRT
<213> ORGANISM: Artificial sequence
<220> FEATURE:
<223> OTHER INFORMATION: Synthetic peptide

<400> SEQUENCE: 38
```

Thr Glu Asp Ser Val Ser Ala Pro Ala Glu Ala Ser Val Val Pro Ala
1               5                   10                  15

Ala Glu Ala Pro Gln Pro Ala Gln Gln Thr Glu Asp Glu Phe Phe Ser
            20                  25                  30

Asp Gly Ile Glu Ala
        35

```
<210> SEQ ID NO 39
<211> LENGTH: 37
<212> TYPE: PRT
<213> ORGANISM: Artificial sequence
<220> FEATURE:
<223> OTHER INFORMATION: Synthetic peptide

<400> SEQUENCE: 39
```

Glu Ala Ser Val Val Pro Ala Ala Glu Ala Pro Gln Pro Ala Gln Gln
1               5                   10                  15

Thr Glu Asp Glu Phe Phe Ser Asp Gly Ile Glu Ala Thr Glu Asp Pro
            20                  25                  30

Val Ser Ala Thr Ala
        35

```
<210> SEQ ID NO 40
<211> LENGTH: 37
<212> TYPE: PRT
<213> ORGANISM: Artificial sequence
<220> FEATURE:
<223> OTHER INFORMATION: Synthetic peptide

<400> SEQUENCE: 40
```

```
Thr Glu Asp Pro Val Ser Ala Thr Ala Glu Ala Ser Val Val Pro Ala
1               5                   10                  15

Ala Glu Ala Pro Gln Pro Ala Gln Gln Thr Asp Glu Phe Phe Ser
            20                  25                  30

Asp Gly Ile Glu Ala
        35

<210> SEQ ID NO 41
<211> LENGTH: 18
<212> TYPE: PRT
<213> ORGANISM: Artificial sequence
<220> FEATURE:
<223> OTHER INFORMATION: Synthetic peptide

<400> SEQUENCE: 41

Thr Glu Asp Ser Val Ser Ala Pro Ala Thr Glu Asp Pro Val Ser Ala
1               5                   10                  15

Thr Ala

<210> SEQ ID NO 42
<211> LENGTH: 18
<212> TYPE: PRT
<213> ORGANISM: Artificial sequence
<220> FEATURE:
<223> OTHER INFORMATION: Synthetic peptide

<400> SEQUENCE: 42

Thr Glu Asp Pro Val Ser Ala Thr Ala Thr Glu Asp Ser Val Ser Ala
1               5                   10                  15

Pro Ala

<210> SEQ ID NO 43
<211> LENGTH: 96
<212> TYPE: PRT
<213> ORGANISM: Ehrlichia canis

<400> SEQUENCE: 43

Thr Glu Asp Ser Val Ser Ala Pro Ala Thr Glu Asp Ser Val Ser Ala
1               5                   10                  15

Pro Ala Gly Gly Gly Ala Ser Val Val Pro Glu Ala Glu Ala Ser Val
            20                  25                  30

Val Pro Glu Ala Glu Gly Gly Gly Glu Ala Ser Val Val Pro Ala Ala
            35                  40                  45

Glu Ala Pro Gln Pro Ala Gln Gln Thr Glu Asp Glu Phe Phe Ser Asp
        50                  55                  60

Gly Ile Glu Ala Glu Ala Ser Val Val Pro Ala Ala Glu Ala Pro Gln
65                  70                  75                  80

Pro Ala Gln Gln Thr Glu Asp Glu Phe Phe Ser Asp Gly Ile Glu Ala
                85                  90                  95

<210> SEQ ID NO 44
<211> LENGTH: 39
<212> TYPE: PRT
<213> ORGANISM: Ehrlichia canis

<400> SEQUENCE: 44

Thr Glu Asp Ser Val Ser Ala Pro Ala Thr Glu Asp Ser Val Ser Ala
1               5                   10                  15

Pro Ala Gly Gly Gly Thr Glu Asp Ser Pro Ser Ala Thr Ala Thr Glu
            20                  25                  30
```

-continued

```
Asp Ser Pro Ser Ala Thr Ala
        35

<210> SEQ ID NO 45
<211> LENGTH: 18
<212> TYPE: PRT
<213> ORGANISM: Artificial Sequence
<220> FEATURE:
<223> OTHER INFORMATION: Synthetic linker

<400> SEQUENCE: 45

Gly Ser Thr Ser Gly Ser Gly Lys Pro Gly Ser Gly Glu Gly Ser Thr
1               5                   10                  15

Lys Gly

<210> SEQ ID NO 46
<211> LENGTH: 5
<212> TYPE: PRT
<213> ORGANISM: Artificial Sequence
<220> FEATURE:
<223> OTHER INFORMATION: Synthetic linker

<400> SEQUENCE: 46

Glu Ala Ala Ala Lys
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic linker

<400> SEQUENCE: 47

Gly Gly Gly Gly Ser
1               5
```